US012433537B2

(12) United States Patent
Petersen et al.

(10) Patent No.: US 12,433,537 B2
(45) **Date of Patent: *Oct. 7, 2025**

(54) HEARING AID COMPRISING ONE OR MORE SENSORS FOR BIOMETRICAL MEASUREMENTS

(71) Applicant: Oticon A/S, Smørum (DK)

(72) Inventors: Svend Oscar Petersen, Smørum (DK); Mathias Bruun Larsen, Smørum (DK); Sergi Rotger Griful, Smørum (DK); José Antonio Esparza Isasa, Smørum (DK); Mikkel Nielsen, Smørum (DK); Kim Mølholm Hejlesen, Smørum (DK); Henrik Bendsen, Smørum (DK); Preben Kvist, København SV (DK); Svend Erik Elgaard, Smørum (DK); Jeanette Bülow Nielsen, Smørum (DK); Zenia Holtzmann Lausten, Smørum (DK); Malte Kiewning, Smørum (DK); Jesper B. Johansen, Smørum (DK); Nicolai Westergren, Smørum (DK); Tanveer Bhuiyan, Smørum (DK); Sudershan Y.S, Smørum (DK)

(73) Assignee: Oticon A/S, Smørum (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,159

(22) Filed: Apr. 18, 2024

(65) Prior Publication Data

US 2024/0268758 A1 Aug. 15, 2024

Related U.S. Application Data

(63) Continuation of application No. 17/571,121, filed on Jan. 7, 2022, now Pat. No. 11,998,354.

(30) Foreign Application Priority Data

Jan. 8, 2021 (EP) .................................... 21150674

(51) Int. Cl.
*H04R 25/00* (2006.01)
*A61B 5/00* (2006.01)

(52) U.S. Cl.
CPC ......... *A61B 5/6817* (2013.01); *H04R 25/505* (2013.01); *H04R 25/554* (2013.01);
(Continued)

(58) Field of Classification Search
CPC .. H04R 25/609; H04R 25/505; H04R 25/554; H04R 25/602; H04R 25/604; H04R 25/652; H04R 2225/021; H04R 2225/55
(Continued)

(56) References Cited

U.S. PATENT DOCUMENTS 11,523,202 B2 12/2022 Au et al.
2017/0311097 A1 10/2017 Nielsen et al.
(Continued)

FOREIGN PATENT DOCUMENTS

WO WO 2019/232042 A1 12/2019

OTHER PUBLICATIONS

European Search Report, issued in EP Application No. 21150674.6, dated Jun. 4, 2021.

*Primary Examiner* — Phylesha Dabney
(74) *Attorney, Agent, or Firm* — Birch, Stewart, Kolasch & Birch, LLP

(57) ABSTRACT

A hearing aid having one or more biometrical sensors, where the hearing aid comprises at least one microphone configured to receive a sound of the surroundings, a signal processor configured to process the sound received from the microphone and a speaker unit configuration configured to
(Continued)

emit the processed sound into the ear of a user, wherein one or more sensors is positioned substantially in the ear together with at least a part of the hearing aid, wherein the one or more sensors is configured as biometrical sensors configured for recording health data of a hearing aid user.

14 Claims, 28 Drawing Sheets

(52) U.S. Cl.
CPC ......... *H04R 25/602* (2013.01); *H04R 25/604* (2013.01); *H04R 25/609* (2019.05); *H04R 25/652* (2013.01); *H04R 2225/021* (2013.01); *H04R 2225/55* (2013.01)

(58) Field of Classification Search
USPC .......................................................... 381/315
See application file for complete search history.

(56) References Cited

U.S. PATENT DOCUMENTS

| | | | | |
|---|---|---|---|---|
| 2019/0253793 | A1 | 8/2019 | Pedersen et al. | |
| 2021/0099815 | A1* | 4/2021 | Silberzahn ........... | A61B 5/6817 |

* cited by examiner

- CONT. -

- CONT. -

HEARING AID COMPRISING ONE OR MORE SENSORS FOR BIOMETRICAL MEASUREMENTS

This application is a Continuation of copending application Ser. No. 17/571,121, filed on Jan. 7, 2022, which claims priority under 35 U.S.C. § 119(a) to Application No. 21150674.6, filed in Europe on Jan. 8, 2021, all of which are hereby expressly incorporated by reference into the present application.

The present disclosure relates to a hearing aid configured with one or more sensors for measuring biometrical signals. In particular the present disclosure relates to a hearing aid configured with one or more sensors within and/or in near proximity to the inner parts of the ear canal. More particularly, a part of the disclosure relates to optimization of the positioning of biometrical sensors in connection with different types of hearing aids to obtain sufficient biometrical measures in an ear canal. Further the present disclosure also concerns the application of sensors and provides a series of suggestions on how to handle the signals obtained by sensors in the ear canal so as to obtain sufficient quality measures of biometrical signals that can be used in relation to a hearing aid and a hearing aid user.

In recent years there has been a growing interest in applying biometrical sensors for obtaining biometrical measurements via a hearing aid having sensors arranged in close proximity to or in connection to at least a part of the ear canal. Research is continuously focusing on finding the optimal positioning and use of biometrical sensors within the ear canal. Dependent on the sensor used, the proximity and/or direct contact between the sensor and the skin of the ear canal may be of importance to obtain sufficient quality measures to be used in further processing and applications within e.g. the hearing aid processing, biometrical signal alerts, health monitoring etc. obtained via a hearing aid.

Some sensors is configured to provide inputs to the audio processing algorithms of the hearing aid, thereby improving the audiology, whereas other sensors intend to monitor general health and wellbeing of the users, given there is an overlap between hearing loss and health challenges due to both increasing with age.

The ear canal does however not increase in size with age. Therefore, the challenge of packaging all of the electronics of a hearing aid at least partly located inside the ear canal must be solved, especially when focusing on in the ear style hearing aids, such as receiver-in-the ear (RITE) type, In the ear (ITE) type, Completely in the ear (CIC) type, custom mold hearing aids etc. An increase in size due to the addition of sensors provided within the volume available in the hearing aids will limit discreteness of instruments/speaker units in addition to fitting fewer users. Another major issue with some sensors is that they require a robust contact to the skin. For e.g. while measuring EEG/ECG, a bad contact of the electrodes can cause the loss of signal or degrade signal quality. A PPG sensor behaves similarly. As it basically measures a change in signal intensity due to absorption during reflectometry, placing the sensor close to the skin will collect as much light as possible due to reflections from the skin to provide strongest signal. A robust contact to the skin will minimize changes in the optical path due to motion and hence provide a cleaner signal. If a contact temperature sensor has physical contact to the skin, the measurement will be dominated by the skin temperature whereas if it is located on the speaker unit in 'free air' it will be affected by the heat discharged (potentially from other sensors) in the speaker unit in addition to the air temperature inside the ear, which will be affected by the ambient temperature and the convection caused by movement (air in canal being swapped by ambient temperature air).

In light of the above, and several other challenges faced when implementing sensors into a hearing aid, this disclosure provides solutions for different types of hearing aids, that addresses the optimal positioning of sensors within the ear canal in a hearing aid context. Furthermore, the disclosure provides solutions for optimizing the signal handling from the different sensors and present some biometrical applications with which at least some of the mentioned sensors can be used. The present disclosure provides at least a plurality of alternatives to existing solutions.

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIG. 1 schematically shows a hearing aid user wearing at hearing aid pair configured to communicate with an auxiliary device;

FIG. 2 schematically shows a hearing aid as an example of a hearing aid according to at least parts of the disclosure;

FIG. 3A schematically illustrates an example of a PPG sensor according to at least a part of the disclosure;

FIG. 3B schematically illustrates an example of a PPG sensor according to at least a part of the disclosure;

FIG. 3C schematically illustrates an example of a PPG sensor according to at least a part of the disclosure;

Figure 13:
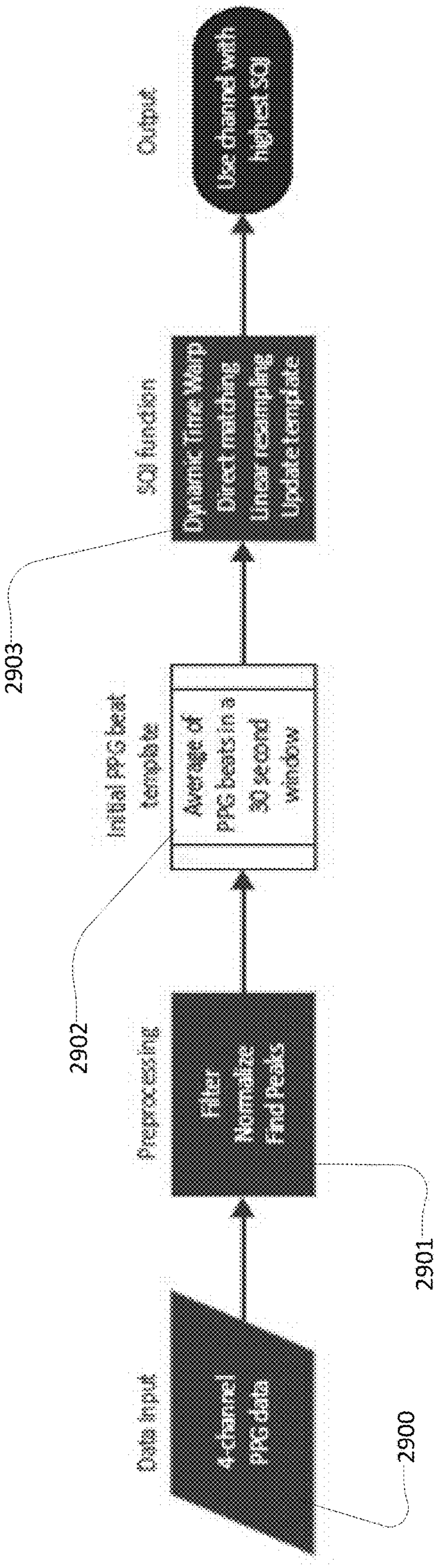
FIG. 13 illustrates example signal processing steps for compensating for noise in a sensor signal, such as an PPG sensor signal.
Figure 13A:
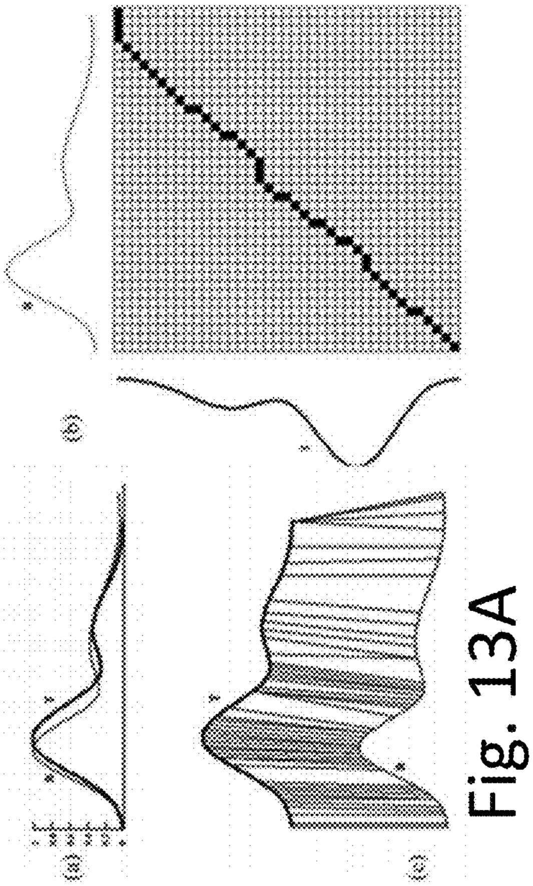
FIG. 13A illustrates parts of the signal processing of FIG. 13.
Figure 13B:
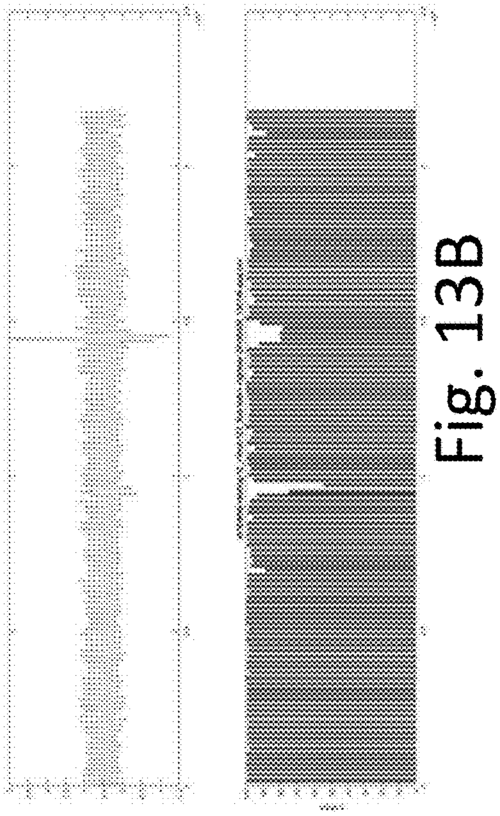
FIG. 13B illustrates parts of the signal processing of FIG. 13.
Figure 13C:
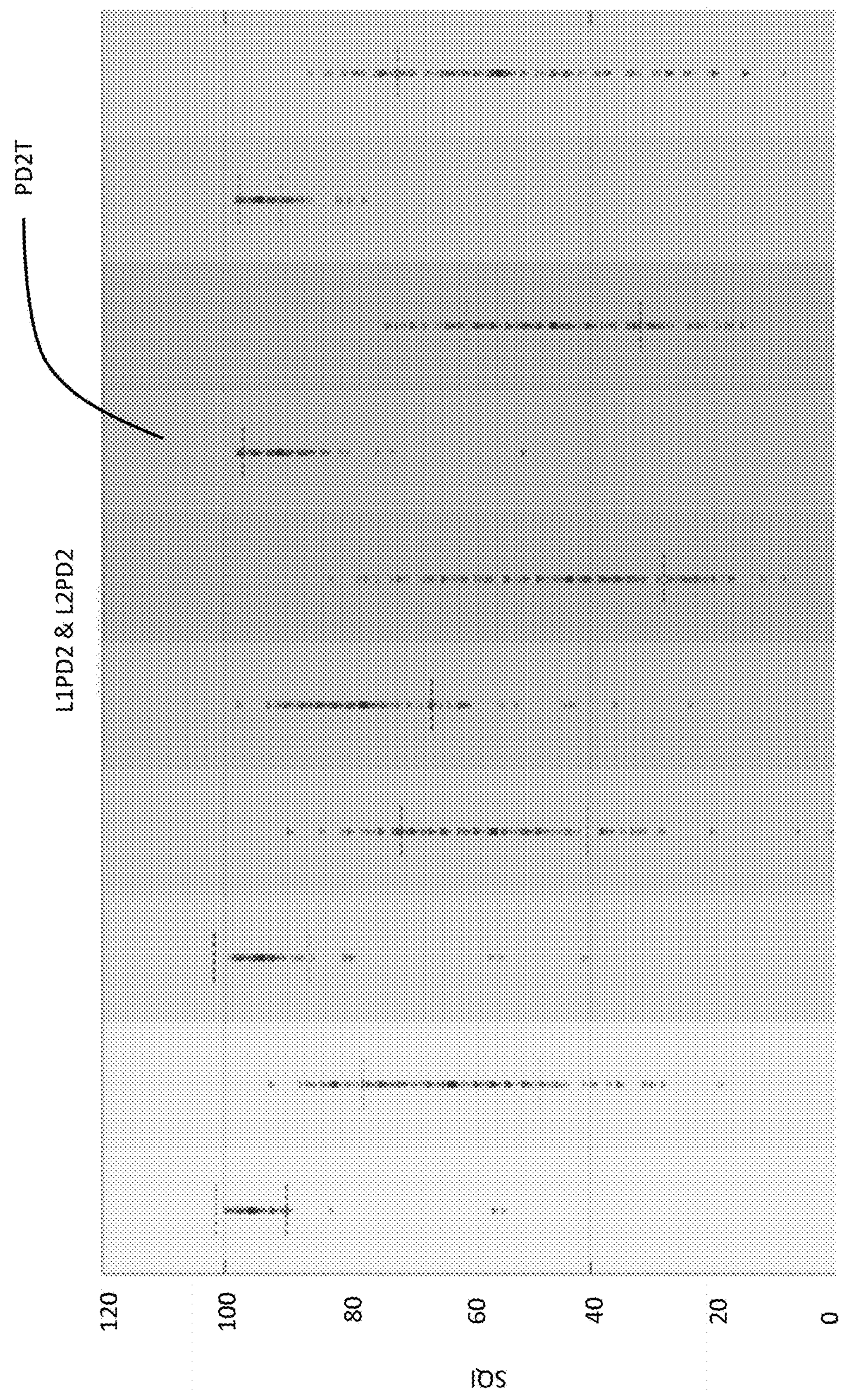
FIG. 13C illustrates parts of the signal processing of FIG. 13.
Figure 13C:
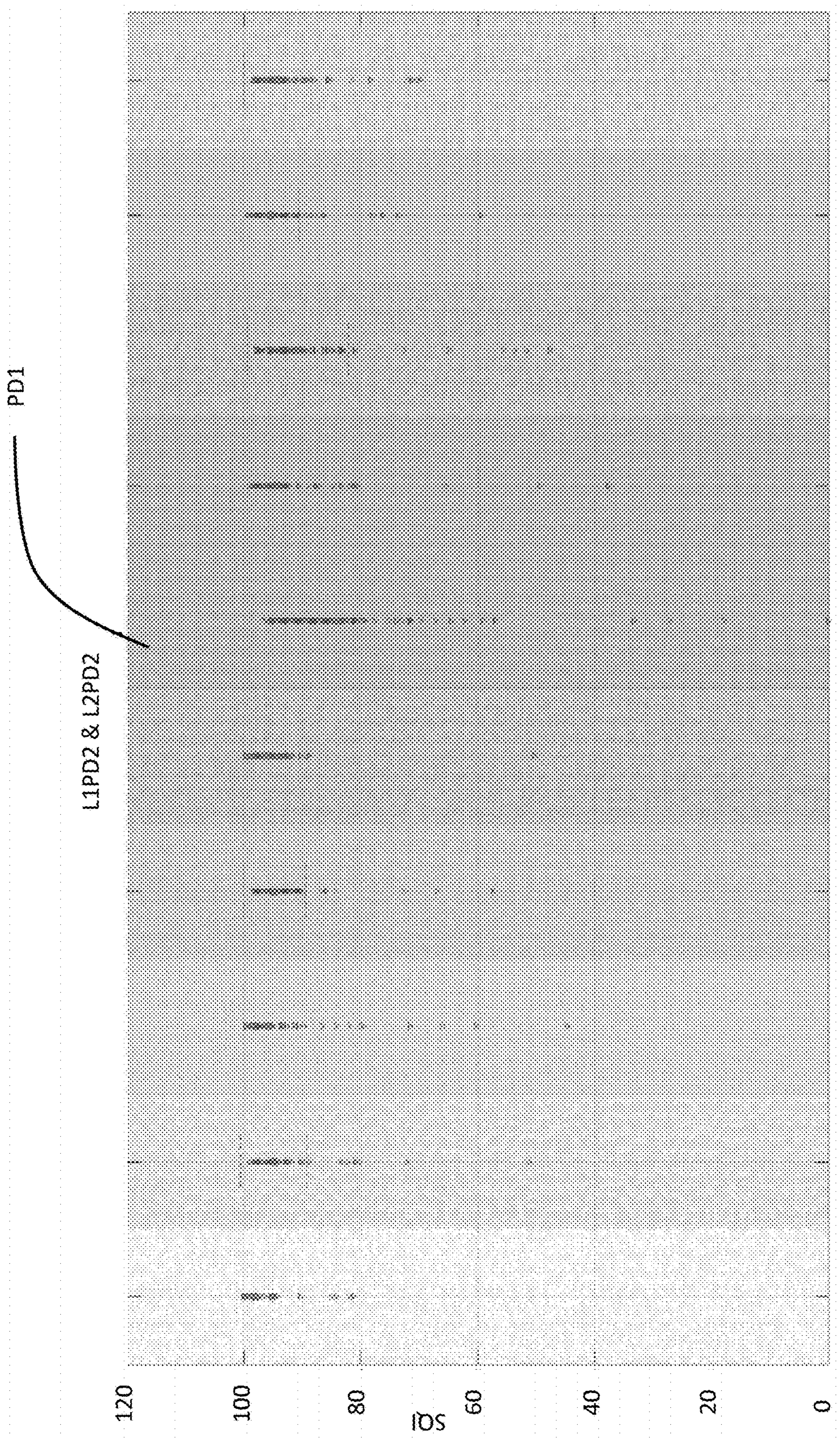
Figure 13D:
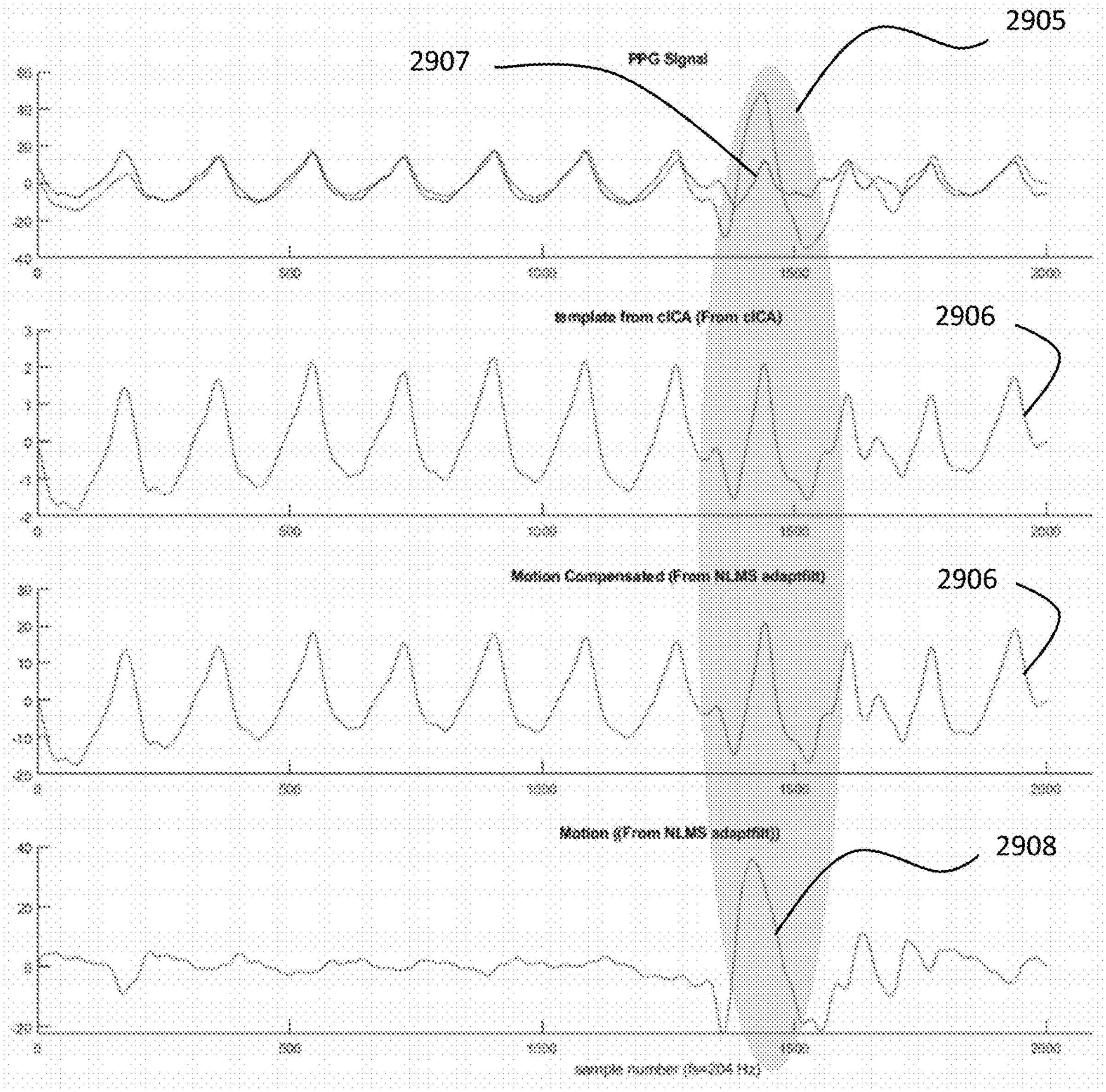
FIG. 13D illustrates parts of the signal processing of FIG. 13 used to compensate for noise in a PPG signal.
Figure 13E:
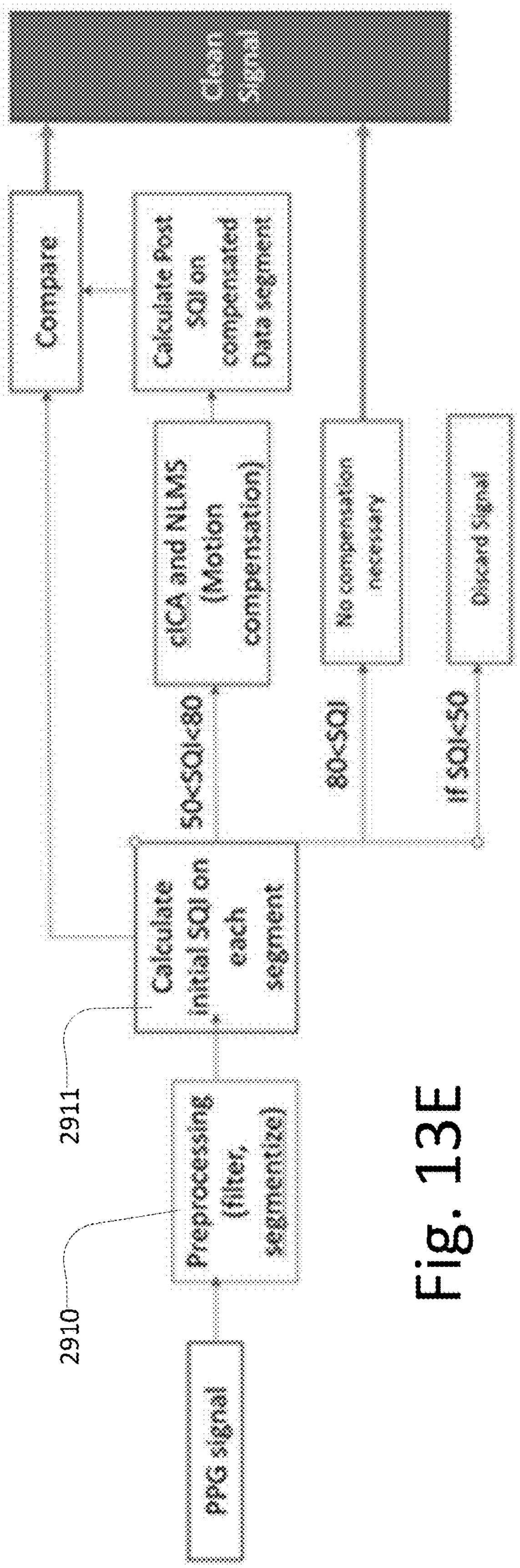
FIG. 13E illustrates a signal process utilized for compensate for noise in a sensor signal in relation to FIG. 13.
Figure 13F:
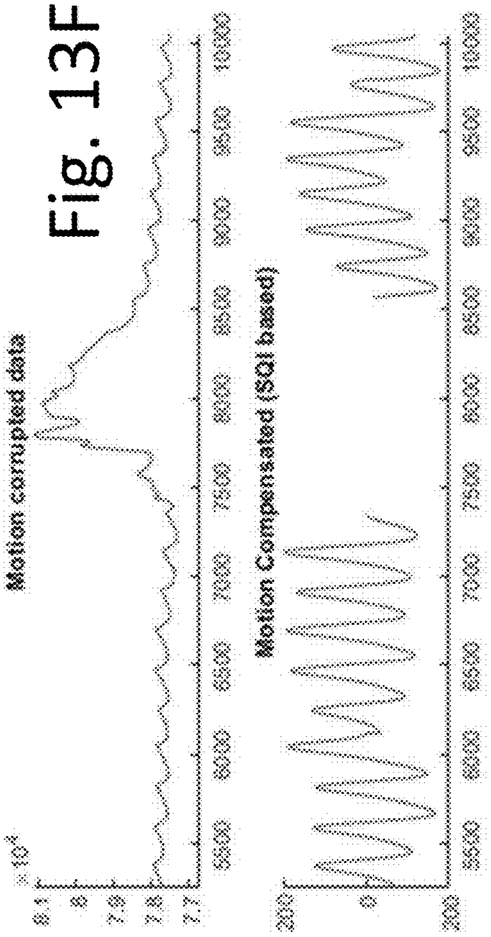
Figure 14A:
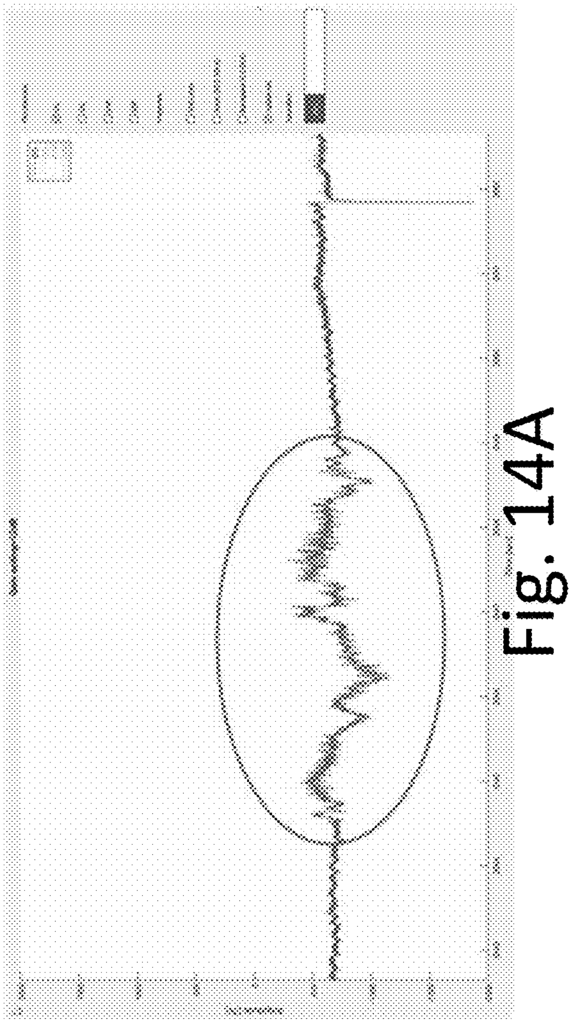
Figure 14B:
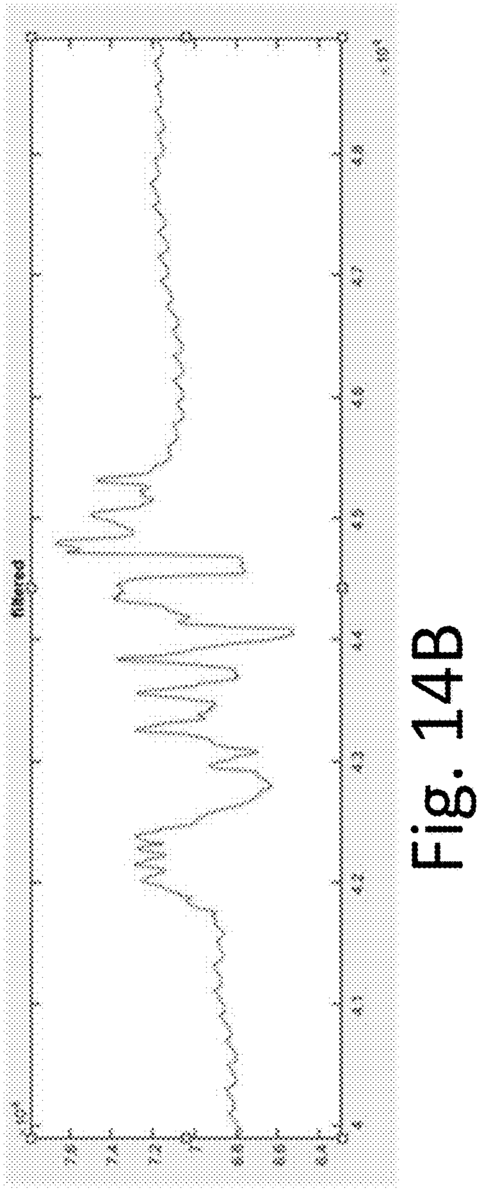
Figure 14C:
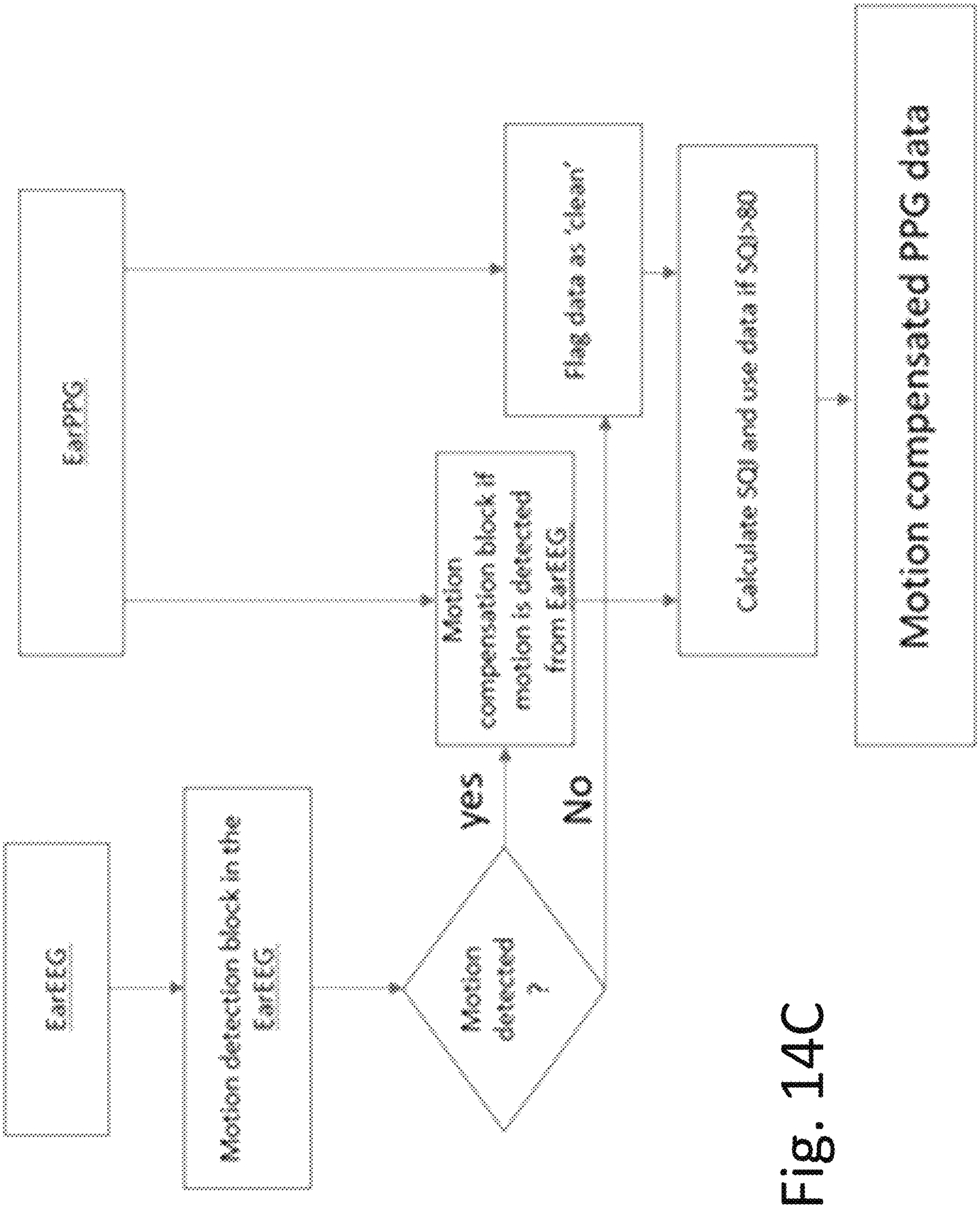
Figure 14D:
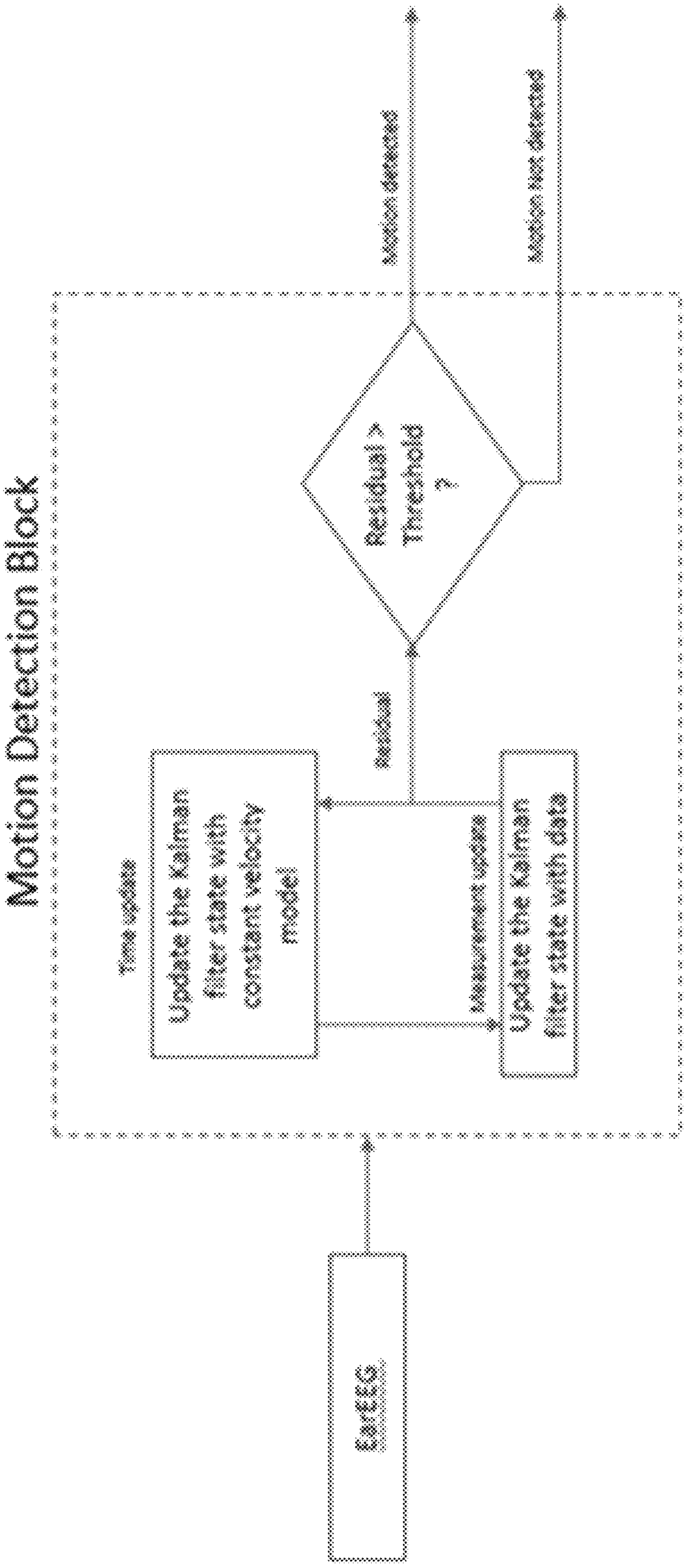

FIG. 13F illustrated a noise compensated signal in accordance with the signal process of FIG. 13E;

FIG. 14A show typical motion artefact induced EarEEG signal obtained within the ear;

FIG. 14B show typical motion artefact induced PPG signal obtained within the ear;

FIG. 14C illustrates a signal process used to motion compensate a PPG data signal;

FIG. 14D illustrates parts of the signal process according to FIG. 14E; and

Figure 15:
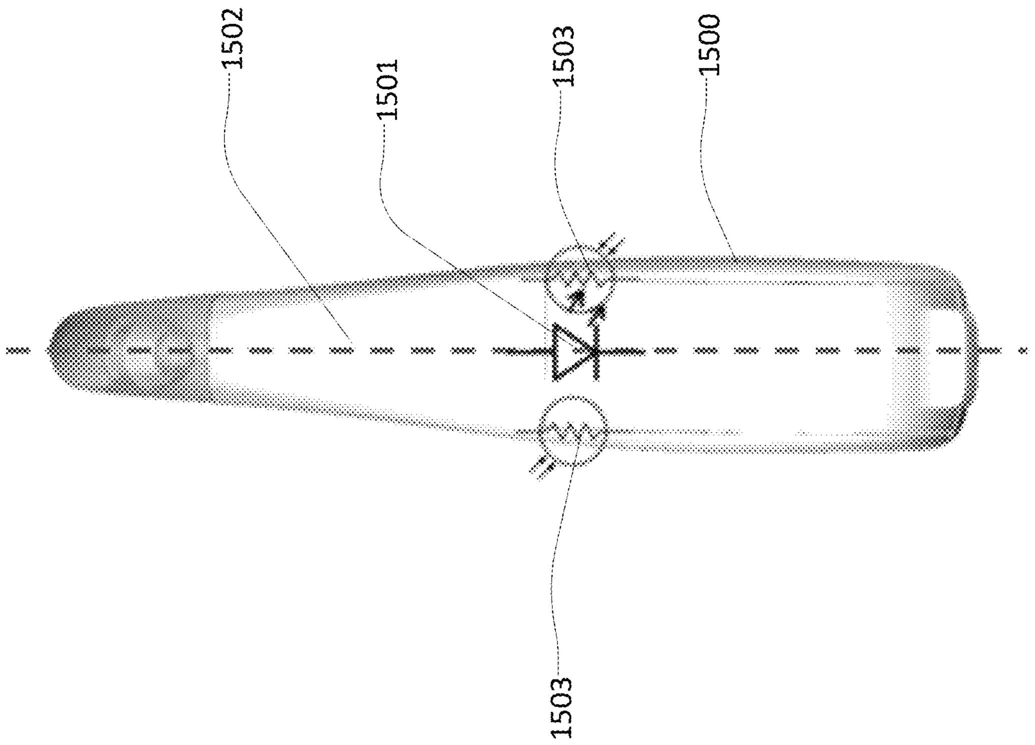

FIG. 15 illustrates a front view of a BTE style hearing aid having a PPG sensor.

The description set forth below in connection with the appended drawings is intended as a description of various configurations. The description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

In general, it should be understood that a hearing device (or hearing instrument, hearing assistance device) may be or include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing device" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal and connected by conductive wires (or wirelessly) to the unit behind the ear, such as in a Behind-the-Ear type hearing aid, and/or ii) arranging the hearing device entirely or partly in the pinna and/or in the ear canal of the user such as in an In-the-Ear type hearing aid or In-the-Canal/Completely-in-Canal type hearing aid, or iii) arranging a unit of the hearing device attached to a fixture implanted into the skull bone such as in a Bone Anchored Hearing Aid or a Cochlear Implant, or iv) arranging a unit of the hearing device as an entirely or partly implanted unit such as in a Bone Anchored Hearing Aid or a Cochlear Implant. The hearing device may be implemented in one single unit (housing) or in a number of units individually connected to each other.

Figure 1:
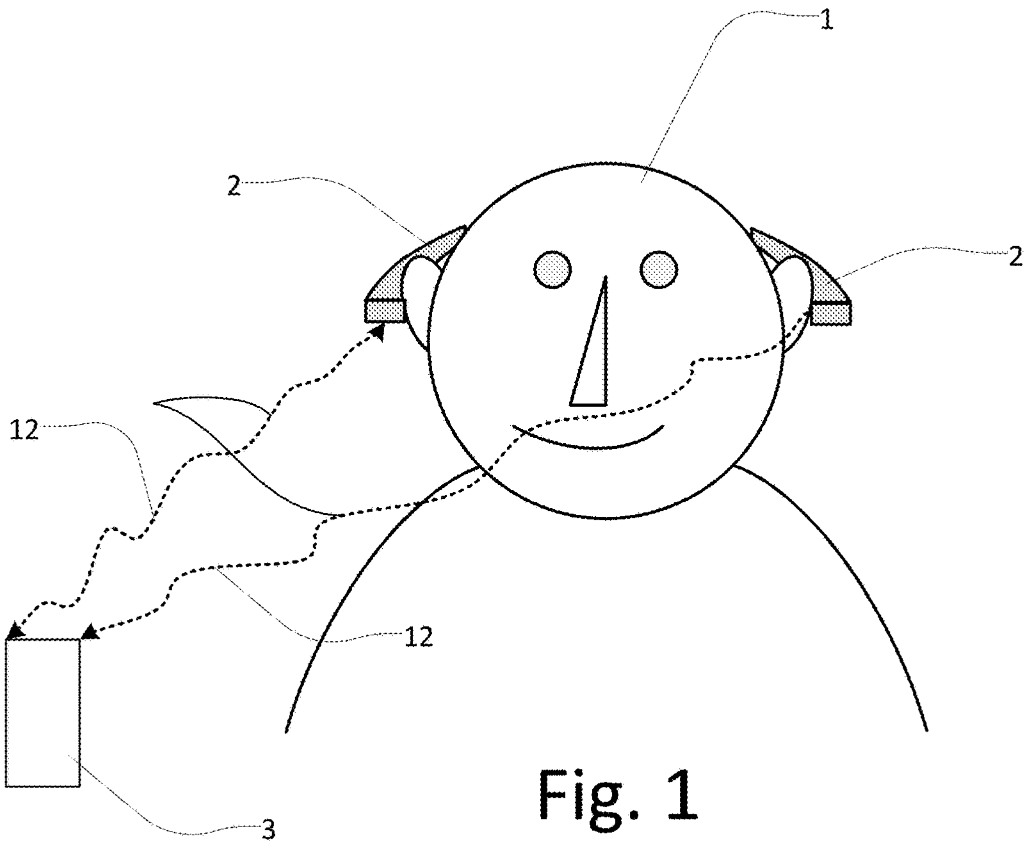

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include one or more auxiliary device(s) that communicates with at least one hearing device, the auxiliary device affecting the operation of the hearing devices and/or benefitting from the functioning of the hearing devices. An example of a hearing system in communicatively contact with an auxiliary device is shown in FIG. 1, where a hearing aid user 1 wearing a hearing aid 2 on each of the ears of the user 1 is illustrated. As illustrated the hearing aids 2 are both configured to communicate with an auxiliary device 3. However, it should be noted that only one of the hearing aids could be configured to communicate with the auxiliary device. The communication between the one or more hearing aids 2 and the auxiliary device may be configured as a wired or wireless communication link between the at least one hearing device and the auxiliary device. The communicative link between the devices is established so as to allow for exchanging information (e.g. control and status signals, possibly audio signals and possible sensor signals) between the at least one hearing device and the auxiliary device. Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing device. The remote control is adapted to control functionality and/or operation of the at least one hearing device. The function of the remote control may be implemented in a smartphone or other (e.g. portable) electronic device, the smartphone/electronic device possibly running an application (APP) that controls functionality of the at least one hearing device. Especially of relevance to this disclosure is that the auxiliary device, when configured e.g. as a smartphone is provided with an app configured to monitor, control, adjust etc. the hearing aid processing and functionality on the basis of sensor data and/or to warn and/or inform a user of e.g. a health state, a cognitive state etc. based on the biometrical data obtained by the sensors in the hearing aid.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a particular part of the microphone signal originates. This may be achieved by using conventionally known methods. The signal processing unit may include an amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

Figure 2:
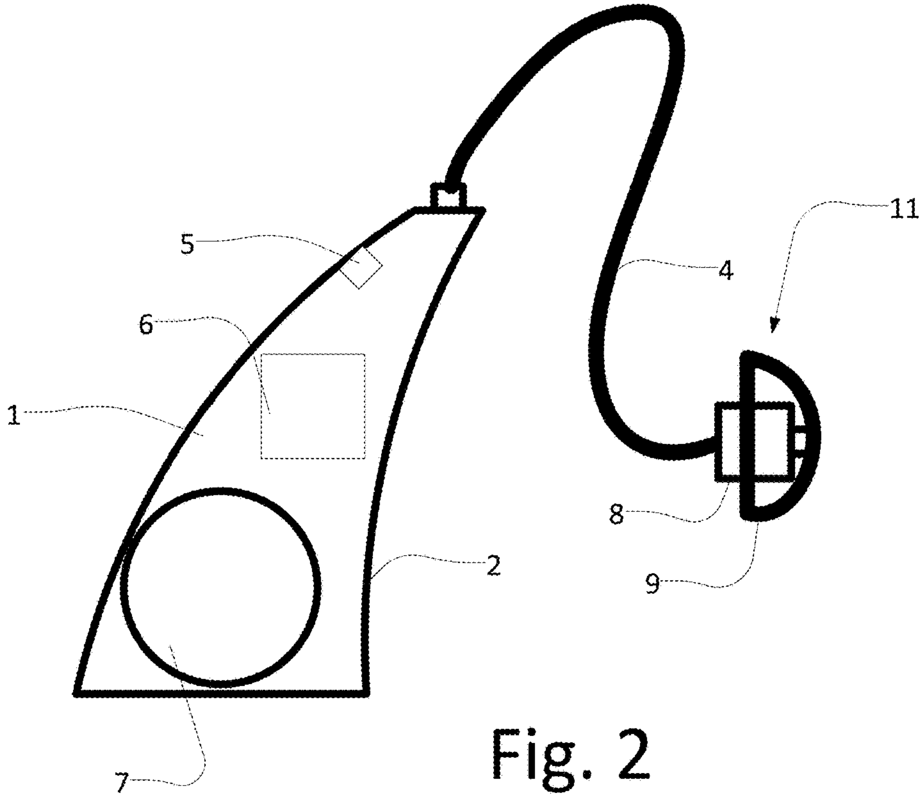

An example of a RITE style hearing aid is illustrated in FIG. 2. This is only given as an example, as it will be clear throughout the disclosure that other styles of hearing aids could also be configured with sensors for measuring biometrical data. The RITE style hearing aid of FIG. 2 generally comprises a behind the ear part 2 comprising a battery 7, a signal processor 6, at least one microphone 5, and a speaker wire 4 connected to the behind the ear part 2. The speaker wire 4 connects in the opposite end of the behind the ear part 2, to a receiver unit 8 configured to be connected with a dome 9 of the hearing aid.

Accordingly, in general, in an aspect of the disclosure, a hearing aid having one or more biometrical sensors is disclosed. The hearing aid comprises at least one microphone configured to receive a sound of the surroundings; a signal processor configured to process the sound received from the microphone; a speaker unit configuration configured to emit the processed sound into the ear of a user. The one or more sensors is positioned substantially in the ear together with at least a part of the hearing aid, wherein the one or more sensors is configured as biometrical sensors configured for recording health data of a hearing aid user, wherein further, the hearing aid comprises a wireless communication interface configured to transmit at least the biometrical signals recorded by the one or more biometrical signals to an auxiliary device. The hearing aid comprises a behind the ear part having said signal processor, a battery and the one or more microphones, wherein the behind the ear part is connected to an in-the-ear part via a wire configured to allow communication between the behind the ear part and the in-the-ear part, wherein the in-the-ear part comprises the one or more biometrical sensors and wherein the in-the-ear part comprises at least one speaker unit configuration, wherein at least a part of the speaker unit configuration is in communication with and/or in direct contact with the one or more biometrical sensors, wherein each of the one or more biometrical sensors is arranged in connection with the speaker unit configuration at a printed circuit board directly at a receiver of the speaker unit configuration or at a printed circuit board in close proximity to or directly connected to the receiver of the speaker unit configuration. As previously mentioned, FIG. 1 and FIG. 2 illustrates examples of a hearing aid according to disclosure with a behind the ear part 10, a wire (also denoted a speaker wire) 4 connecting the behind the ear part 10 with the in-the-ear part 11. The wireless communication interface is indicated by arrows 12 which illustrates that a communication between the hearing aid 2 and the auxiliary device 3 exist. The internal parts, such as how the sensors are arranged in connection with the speaker unit configuration 8 will be apparent throughout the disclosure. Further the speaker unit configuration should be contemplated to be understood as a unit of the hearing aid comprising the receiver (also denoted a speaker) of the hearing aid together with other among other features, electrical components, PCB etc. of the hearing aid.

In the following different kinds of sensors that can be used with hearing aids is discussed. It should be understood that the sensors described can be used in any of the constructional embodiments described herein, even though specific embodiments may only mention one type of sensor.

Biometrical Sensor Types

Generally speaking, different kinds of sensors may be considered for use in hearing aid applications. A selection of these includes optical heart rate sensors, vibration sensors, Galvanic skin response (GSR) sensors, electroencephalogram (EEG) sensors, Electrocardiogram (ECG) sensors and Auditory brainstem response (ABR) sensors. The different sensors may be used for measuring a plurality of different biomedical signals, which is processed to get a biometrical measure of the current state of a person wearing a hearing aid. The processed sensor signals may in some cases be used to control a hearing aid setting and/or in other cases to warn a patient about a health state that the patient is currently approaching and/or is already in. In the following, examples of applications using different sensors will be explained. It should be noted that the configuration of the different sensors as described in the following in connection with the positioning in the hearing aid could be used in connection with other sensors than the below described solutions.

Optical Heart Rate Sensor

An optical heart rate (OHR) sensor comprises an LED emitter configured to emit light onto the tissue at which the optical heart rate sensor is positioned in close proximity to. The reflected signal detected by the optical heart rate sensor from the skin is a measure of the changes in volume of the blood flow through the tissue that the detector is placed upon. Thus, as the heart beats, the volume of blood circulating in the skin will change, and it is this change that the OHR sensor detects. This means that a high blood volume of the tissue in close proximity to the OHR detector will cause less light to return to the optical sensor, whereas a low blood volume increases that amount of detected light. A measure of the time between high and low intensities enables the OHR sensor to measure the intervals between each hear beat and therefrom calculate the heart rate data. An OHR sensor is also generally known as a PPG sensor example, as will be apparent throughout the disclosure.

Besides measurements of the heart rate of the user, a plethora of other parameters, which are related to the health state of the user, are deducible by this method. For example, the heart rate variability can be measured as an indicator for the physical and psychological stress load, to which the user is exposed. Furthermore, the absolute value of the oxygen concentration in blood can be measured as an indicator for the general health state of the user, based on the phenomenon that oxygenated blood has different absorption characteristics than oxygen-depleted blood at specific wavelengths. Other techniques provide estimations of the blood glucose, for example, thus providing valuable information for diabetics, or estimations of the blood pressure. These various possibilities have made photopletysmography popular not only for users suffering from cardio-vascular diseases, but also for health-conscious users pursuing a healthy lifestyle such as sportspersons and competitive athletes.

That is, an optical heart rate sensor is in a broader perspective known as a PPG (PhotoPlethysmosGram) sensor, which comprises light emitting diodes (LED's) which emit light in all directions. Such sensors, as explained throughout the disclosure, are generally considered for in-ear measurements of biometrical signals in a hearing aid setup. However, the "all directions" emission of the LEDs in a PPG sensor has the drawbacks that:

- Some of the light will be reflected from the top layer surface of skin, i.e. not containing the relevant deeper layer tissue reflection, and therefore will represent noise in the measured reflection.
- A considerable part of the energy form the LED is lost by simple radiation in directions not recorded by the PPG detector. Therefore, only a low amount of the light from the source will propagate through the tissue and effectively reach the detector. Currently a 'brute force' approach is used in PPG sensors, where an extra bright source is used to ensure that more light will end up in the detector. This solution is, however, not feasible in an ultra-low power application such as a Hearing Instrument (HI).

There is therefore a need for a PPG solution for hearing aid applications where the signal loss arising to the above mentioned drawbacks is minimized. The signal is therefore attenuated more, requiring a higher light intensity. These known phenomena causes light to shine in the wrong direction, and skin surface reflections going directly into detector.

To solve the above mentioned problems, one solution may be to place the PPG at an angle within the hearing aid, such that the LED and detector is placed angled therein. This however has been found to worsen the radiation loss as the light must progress further through the skin to reach the detector.

In view of the above mentioned disadvantages connected with the known PPG sensor solutions, it has been necessary to find a solution that solves these disadvantages. This is for example achieved as suggested in the following, by providing a PPG sensor, where the focusing of the light is concentrated in one direction by means of an optical media, or guide arranged within the PPG sensor. Thus, in an embodiment, the hearing aid is configured with at least one biometrical sensor that is configured as a PPG sensor comprising a LED emitter emitting light onto a tissue of the ear canal and a detector detecting reflected light from the tissue of the ear canal, wherein the PPG sensor is configured with at least one optical media in connection with the LED and/or the detector, wherein the optical media focus the emitted and/or detected light, wherein the optical media is arranged substantially in front of the LED emitter and/or detector of the PPG sensor. Such solution increases the effective area of the photo detector and reduces the energy consumption of the emitting diode. The solution is an optical media arranged in front of the LED and/or detector. The function of the optical the media is to focus the light on a given area (e.g. on the photo detector) or in a certain direction (e.g. LED light shines in the direction of the photo detector). Examples of optical media could be lenses and/or optical wave guides. This differs from current implementations, as the optical media used are wavelength filters. A lens or wave guide results in a focus of light from the LED in a more controlled direction and area. The chosen area could be such that the chosen area statistically allows more of the light scattering under the skin (hitting blood vessels thereby generating signal) to return to the detector. Thereby, the light shining in directions, not seen by the detector, will be lessened i.e. less of the energy is wasted by not being picked up.

A similar solution could be used for the photo detector as the lens or wave guide could be used to either widen the viewing area; giving a larger effective area of the photo detector. Alternatively, it could be used to shape the viewing area in a way that less of the directly reflected light from the surface of the skin is seen (or potentially a combination), thereby reducing some of the 'noise' yielding a higher signal to noise ratio.

Thus, combining the two mentioned solutions for the LED and detector (or just using one) will enable the placement of the light source and receiver closer together (or provide more freedom in the mechanical design) due to the more controlled light path. This increases design freedom and/or potentially increases the amount of signal received. The reason being that light does not need to travel as far through the skin (as when spaced farther away or at an angle), which attenuates the signal of interest, to reduce direct skin reflection. Placing the LED and detector closer will increase the portion/probability of the tissue scattered light from the LED (signal of interest) hitting the receiver, due to smaller scattering area in the tissue; i.e. less of the light will have exited the tissue the closer to the source (LED).

Figure 3A:
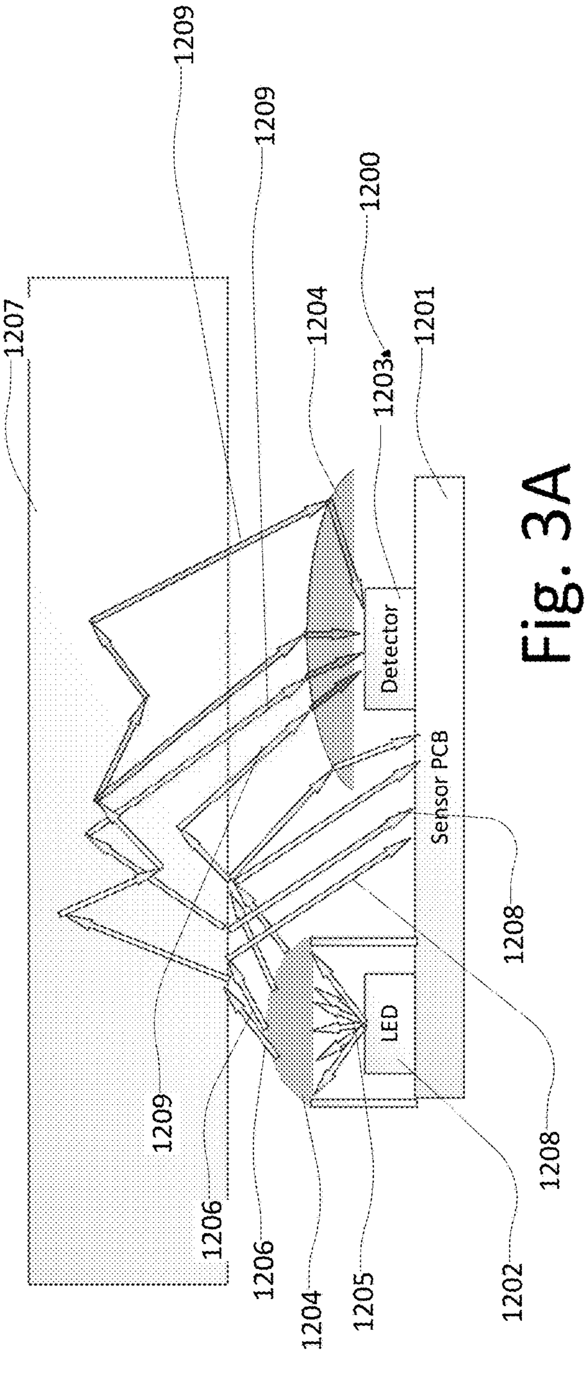

In more detail, and as illustrated in FIG. 3A, the suggested solution is to provide a PPG sensor 1200 comprising a sensor PCB 1201 to which a LED 1202 and a detector 1203 is connected. As illustrated the LED 1202 is configured to emit light 1205, illustrated by the plurality of arrows leaving from the LED sensor 1202. The light 1205 emitted enters into an optical media 1204, which is configured to focus the emitted light into a common direction, as illustrated by arrows 1206 (4 arrows indicates this focused light), leaving the optical media 1204. As illustrated the focused light enters into the tissue 1207, from where it scatters in multiple directions (illustrated by arrows in the tissue 1207). Further, parts of the emitted light 1206 will not enter the tissue but be directly reflected off from the surface of the skin as illustrated by arrows 1208. As indicated in the FIG. 3A it is, as previously explained only the light reflected from the tissue (i.e. indicated by arrows 1209) which are of interest to be detected, since all other non-tissue reflections are mere noise in the detected signal. Therefore, the detector 1203 may also be configured with an optical media 1204, which ensures that light reflected from the tissue will enter into the detector 1203, while leaving out any noise signals from e.g. skin reflections.

Thus, in short, by providing the PPG sensor 1200 with one or more optical medias for centering the light emissions and/or detections to specific areas and directions, it is ensured the noise signals from irrelevant reflections, such as skin is forming part of the detected signal by the PPG sensor.

Figure 3B:
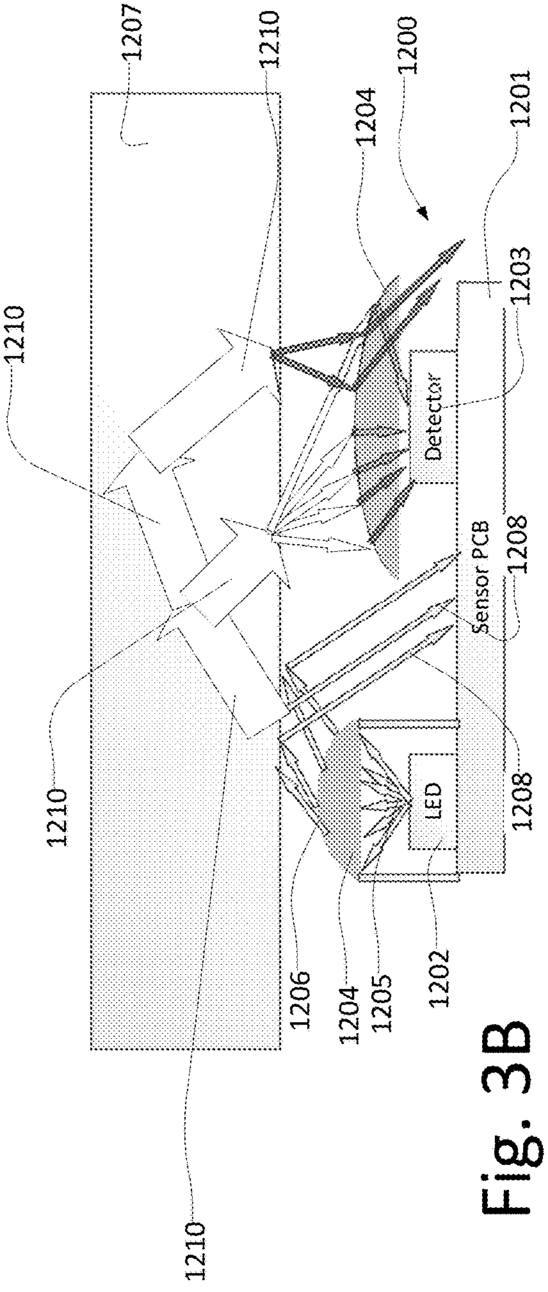
Figure 3C:
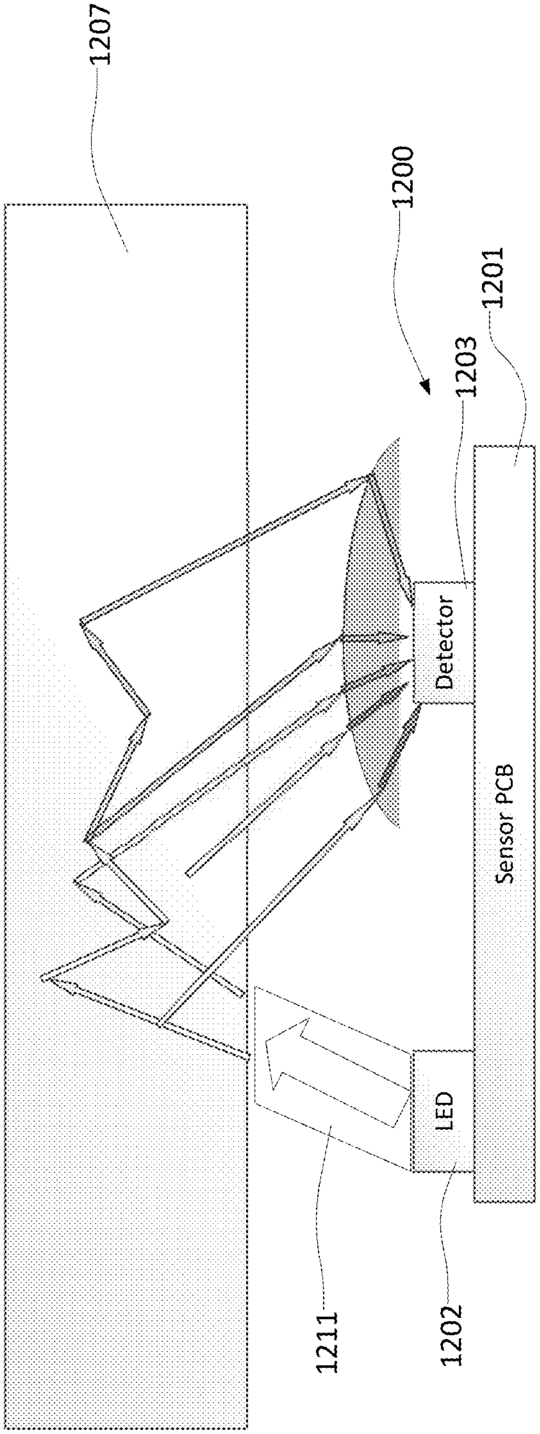

Other possible solutions, which are similar to the just described is illustrated in FIG. 3B and FIG. 3C, why the numbering adhered to the same features as in FIG. 3A will be repeated.

In the embodiment illustrated in FIG. 3B, the main focus is to reduce ambient light and skin reflection concerns. In comparison to FIG. 3A, the difference is that the lens shape (i.e. the optical media 1204) is changed in shape, in or der to 'magnify' a specific area of the emitted light instead of widening the view of the detector. The magnification is illustrated by the larger arrows 1210 entering the tissue 1207, i.e. a more concentrated light.

In another embodiment illustrated in FIG. 3C, the concentration of light entering into the tissue 1207 is focused via a light or wave guide 1211 instead of a lens for the LED (a similar solution could be applied for the detector). The light or wave guide 1211 is configured to focus the direction at which the light hits the skin, again reducing wasted light and light reflecting from the surface towards the detector 1203. Had the detector also used a wave guide the shape would determine if one specific area was measured (like the case 'focus' case above) or if it was wide in the end in contact with the skin it could work to increase the effective area (as the first figure in this solution section).

In general, the proposed solutions, as illustrated and described in relation to FIGS. 3A, 3B and 3C lessens the impact of the sensor not having skin contact, due to the more controlled light path. Skin contact can be hard to realize and/or may be uncomfortable for the user in a hearing aid setting. The advantages it brings can be summarized to: The focusing of light will reduce power consumption, greatly beneficial to hearing instruments (tight power budget), as more energy from the LED will end up in the detector; The lower restriction on skin contact increases the mechanical freedom, in regards to detector/emitter placement, which is very suitable for the ear canal. The reduced skin contact requirement will also improve comfortability for the user. This is also suitable for devices worn all day, like a hearing instrument.

One application for all of the embodiments described in e.g. FIG. 3A, FIG. 3B and FIG. 3C could be to measure blood flow via Doppler shift in laser light. As Doppler shift is important it could be beneficial to focus on a single small exit area of the skin, as other areas would have a different tissue scattering pattern, and therefore a different Doppler shift. Focusing on one area would reduce signal contribution from areas not having the same Doppler shift and therefore yield a cleaner signal.

Galvanic Skin Response (GSR) Sensors

Electrodermal activity (EA) is measured by a galvanic skin response (GSR) sensor, which is a sensor that measures the changes in electrical (ionic) activity resulting from changes in sweat gland activity and it comprises electrodes that are sensitive to these changes, and able to transmit that information a processor. The GSR sensor type is generally speaking an electrode comprising an Ag/AgCl (silver-chloride) contact point with the skin, where the Ag/AgCl are able to accurately transmit the signal from the ionic activity. In general, the GSR sensor measures a change in phasic activity, which signal is transmitted for processing in a signal processor. Normally a significant change in the phase activity response, referred to as an Event-Related Skin conductance response (ER-SCR) or GSR peaks, indicates information about emotional changes to a stimulus. Thus, in a hearing aid setup configuration, where a GSR sensor is positioned in the hearing aid, the GSR sensor may be used to measure a body response to e.g. stress caused by e.g. a difficult to hear situation such as increasing listening effort.

Electrode Type Sensor

Several kinds of electrode sensors exist which are configured for detecting different types of electrical signals of the human being, especially brain activity, heart activity etc. The different types of sensors within the group of electrode sensors includes:

- Electroencephalogram (EEG) sensors that are sensors used to monitor electrical activity of the brain. EEG sensors is typically non-invasive and are in a hearing aid setup used to be positioned in close proximity to the skin of the ear either in the ear canal or at other relevant skin areas of the ear.
- Electrocardiogram (ECG) sensors is an electrode type sensor used to monitor the heart of a patient. ECG sensors are used to collect electrical signals generated by the heart. This allows us to understand the level of physiological arousal that someone is experiencing, but it can also be used to better understand someone's psychological state.

As previously mentioned, all of the described sensor types can be implemented into hearing aids of different styles, such as RITE-styles, CIC-styles, domes of the hearing aids, custom molds etc. In the following a chosen selection of suggested implementations according to this disclosure will be described.

Further, it should be noted that the one or more sensors mentioned herein is configured as sensor configurations that are implemented into the hearing aid. That is, the sensor configuration should be understood to be components of sensors that are arranged in the hearing aid to work together to form a biometrical sensor able to record biometrical signal data. The sensor configuration described herein is chosen at least from the group of biometrical sensors including optical heart rate sensors, galvanic skin response sensors, electroencephalogram sensors, electrocardiogram sensors, accelerometers and wherein at least a part of the sensor is positioned in close proximity to the ear canal or in the inner parts of the ear canal and arranged within parts of a hearing aid as described herein.

In Ear Sensor

Figure 4A:
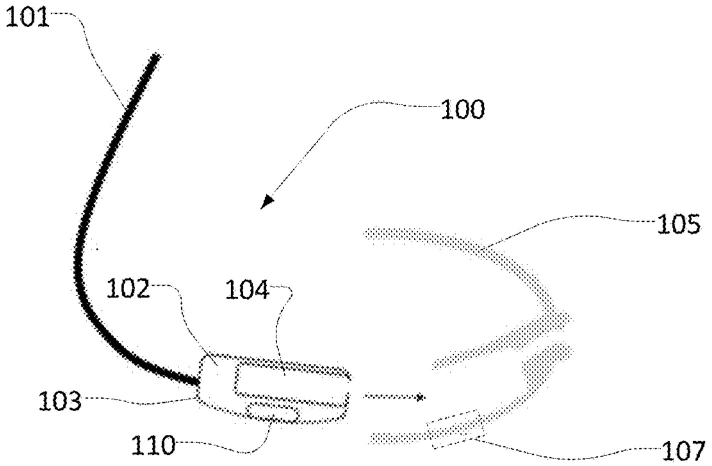
FIG. 4A illustrates an example RITE style hearing aid comprising at least one sensor in a demounted state from the dome of the hearing aid.
Figure 4B:
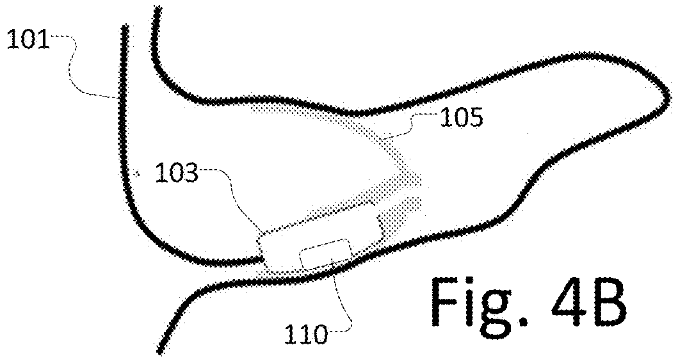
FIG. 4B illustrates an example RITE style hearing aid according to FIG. 4A in a mounted state with the dome of the hearing aid.
Figure 4C:
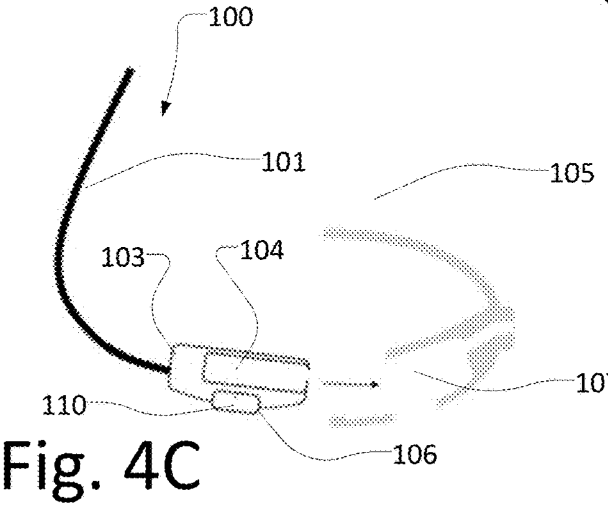
FIG. 4C illustrates an example RITE style hearing aid comprising at least one sensor protruding from the receiver and in a demounted state from the dome of the hearing aid.
Figure 4D:
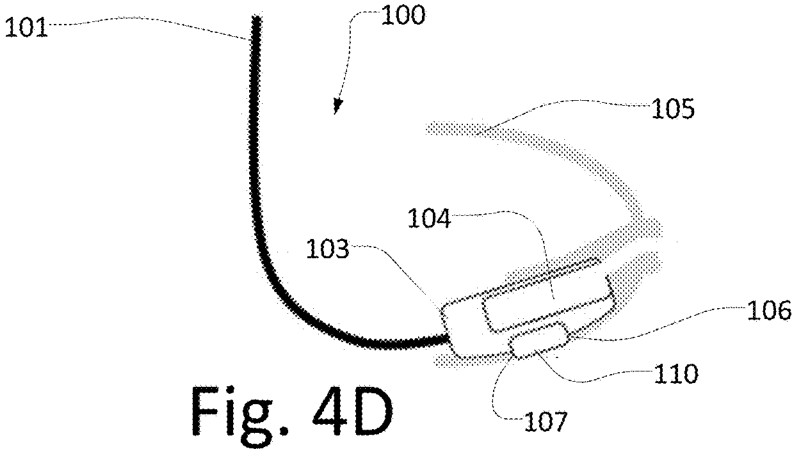
FIG. 4D illustrates an example RITE style hearing according to FIG. 4C in a mounted state with the dome of the hearing aid.

In one embodiment the one or more biometrical sensors is positioned in connection with the speaker unit configuration of the hearing aid, wherein the speaker unit configuration is configured to be mounted to a dome of the hearing aid, wherein the dome comprises a communicative area having at least a material thickness and/or material configuration allowing the one or more sensors to be in communicative contact with the skin of the ear canal, when the speaker unit configuration is inserted into the dome and into the ear canal of a user. Accordingly, in a RITE style hearing aid, as illustrated in FIG. 4A and FIG. 4B, and illustrated with the example of an OHR sensor 110, the sensor 110 may be positioned in a part of the hearing aid, more specifically as illustrated in the Figure, the OHR sensor is here positioned in the receiver unit of the hearing aid, also known as the in-the-ear housing or simply speaker unit or also denoted the speaker unit configuration. Accordingly, in this embodiment the hearing aid is illustrated as a part of a receiver in the ear (RITE) style hearing aid 100, comprising a speaker wire 101 connecting a behind the ear part (not illustrated) to a speaker unit 102 having a speaker 104 and a sensor, in this case the OHR sensor 110, positioned therein. The speaker unit 102 comprises a casing 103 made from a metal or plastic material, which substantially contains the speaker 104 and OHR sensor 110. The speaker unit 102 is as illustrated by the arrow in FIG. 4A configured to be inserted into a dome 105 of the hearing aid.

In more detail, the speaker unit 102 and the dome 105 is configured such that the OHR sensor 110 when inserted into the dome is in communicative contact with the skin of the ear canal. This is achieved since the casing 103 of the speaker unit 102 is configured with an opening 106 through which the OHR sensor extends, thereby leaving the OHR sensor 110 exposed to the surroundings of the speaker casing 103. In a similar manner, the dome 105 of the hearing aid is configured with a communicative area 107 having at least a material thickness and/or material configuration allowing the OHR sensor 110 to be in communicative contact with the skin of the ear canal, when the speaker unit 102 is inserted into the dome 105, as illustrated in FIG. 4B. In this way it is ensured that the light emitted by the LED of the OHR sensor is in direct contact with the skin without any substantial interference and that the reflected signal from the blood flow in the tissue can be detected in the OHR sensor, also without any substantial interference to the signal, thus ensuring an optimal signal emission and detection. The signal detected by the OHR sensor is transmitted to a biometrical signal processor 108 of the speaker unit which is configured to either directly transmit the detected signal to an auxiliary device and/or to transmit the detected signal via a processor in the behind the ear part of the hearing aid to an auxiliary device.

Figure 4E:
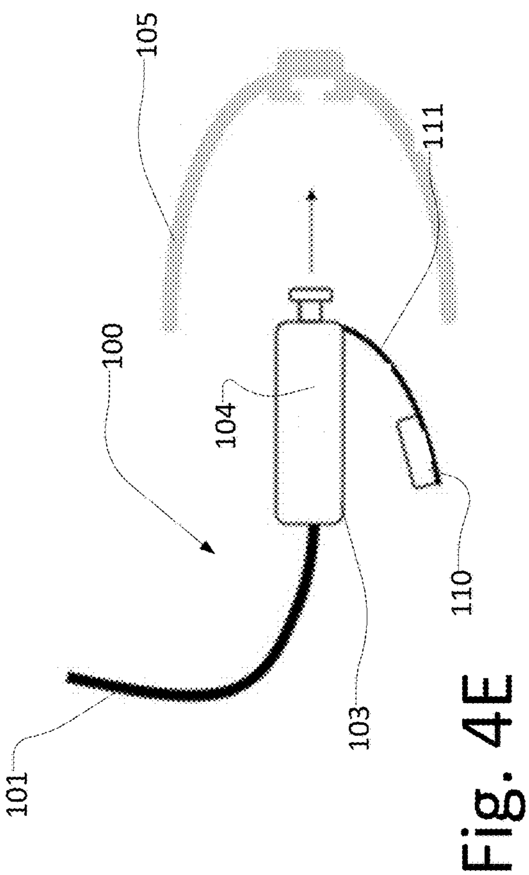
FIG. 4E illustrates an example RITE style hearing aid comprising a sensor on a flexible member an in a demounted state form the dome of the hearing aid.
Figure 4G:
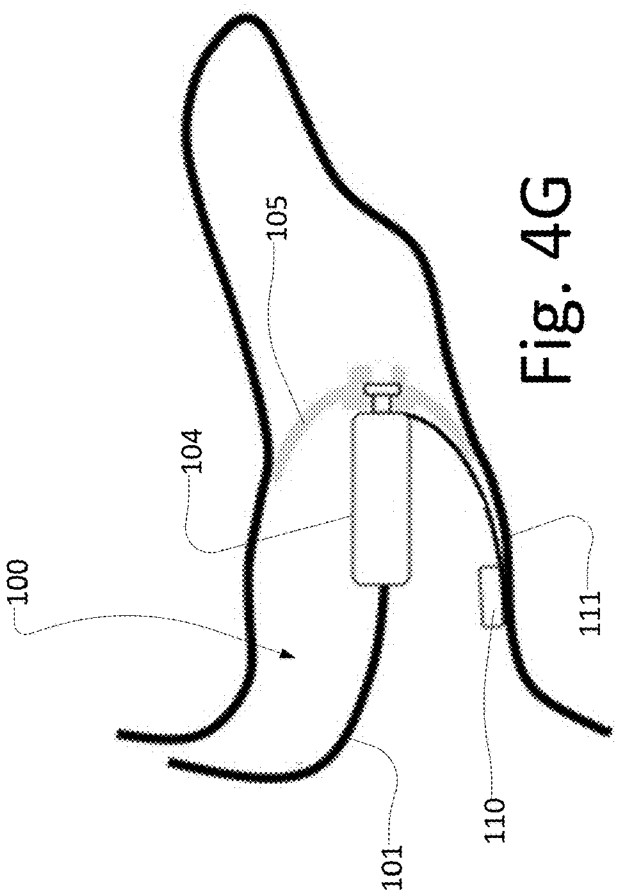
FIG. 4G illustrates an example RITE style hearing aid according to FIG. 4E, where the flexible member extends out from the dome when mounted therein.
Figure 4F:
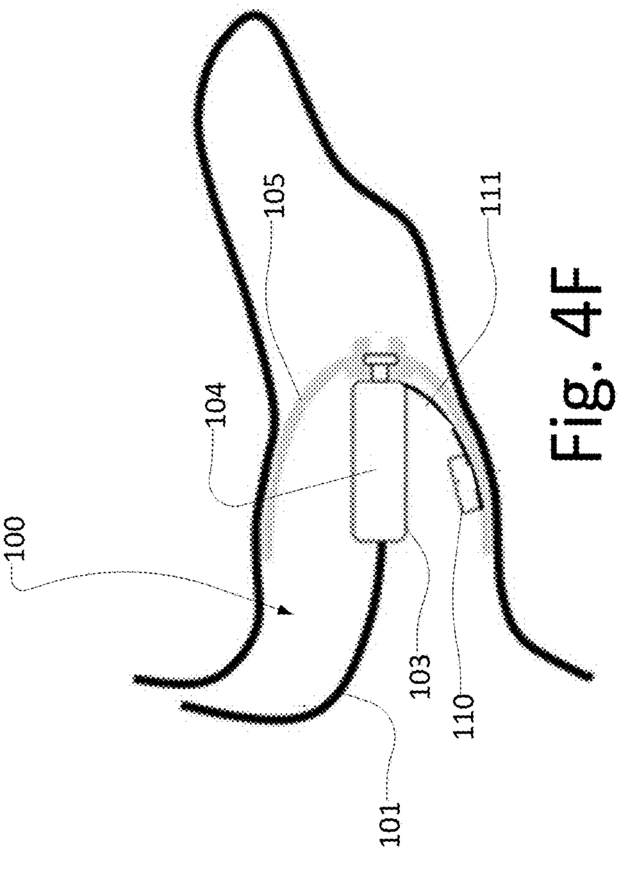
FIG. 4F illustrates an example RITE style hearing aid according to FIG. 4E in a mounted state with the dome of the hearing aid.

Another similar embodiment is illustrated in FIG. 4E and FIG. 4F. Here the receiver unit 103 comprising the speaker 104 is configured with a substantially flexible member 111 extending from a part of the speaker unit 103. The flexible member comprises a sensor 110 or a plurality of sensors, such as an OHR sensor, vibration sensor, EEG sensor, PPG sensor etc. which is attached to the flexible member 11. The flexible member is configured as a communication channel (i.e. electrical transmission), which transmits the signals recorded by the sensor to a processor of the hearing aid. The flexible member, when inserted into the dome together with the receiver unit 103, as illustrated in FIG. 4F is configured to fit into the dome 105, where the dome as previously described is configured with a sensor communicative area allowing the sensor to be in communicatively contact with the skin of the ear canal. Further, in an embodiment illustrated in FIG. 4G, the flexible member 111 may be configured so as to extend outside the borders of the dome 105 and thereby be in direct contact with the skin of the ear canal.

In one example the detected signal from the OHR sensor may be processed to get a measure of the heart rate variability (HRV), which is defined as the variance in time between the beats of your heart. This HRV measure may be used in listening test of hearing aid users, where the user is to rate listening effort while the HRV is measured. Research has shown that that a decreasing HRV is related to situations with hight listening effort which indicates a higher stress load in such situations.

Further in e.g. a RITE style hearing aid as the one just described, a GSR sensor could also be used. That is, referring now to the Figures generally illustrating and describing a RITE style hearing aid, the sensor previously described in relation to e.g. FIGS. 4A, 4B, 4C, 4D, 4E, 4F and 4G could also be configured as a GSR sensor, which preferably also should be arranged to be in communicative contact with the skin within the ear canal. Thus, the same description substantially applies to this type of sensor as described in relation to the OHR sensor.

Dome Sensor Construction

In the previous presented Figures (and in later discussed examples), the biometrical sensors were positioned in relation to the speaker unit of the hearing aid which is merely one way of provided sensors into a hearing aid. In other solutions, were a few examples will be explained in the following, the sensors may be incorporated into the dome material of the hearing aid.

Accordingly, in some embodiments, it is envisioned that the dome could be configured with a dry-contact electrode technology, which has opened the possibility to record bioelectric signals from the ear with the instant fit of electrodes in the ear. However, this at the moment requires a custom made earpiece for each user to ensure optimum contact between the electrodes in the ear. While this is feasible, it restricts the use of biosignal recordings to each individual and may introduce an additional cost for the manufacture of individualized ear-pieces.

Figure 5B:
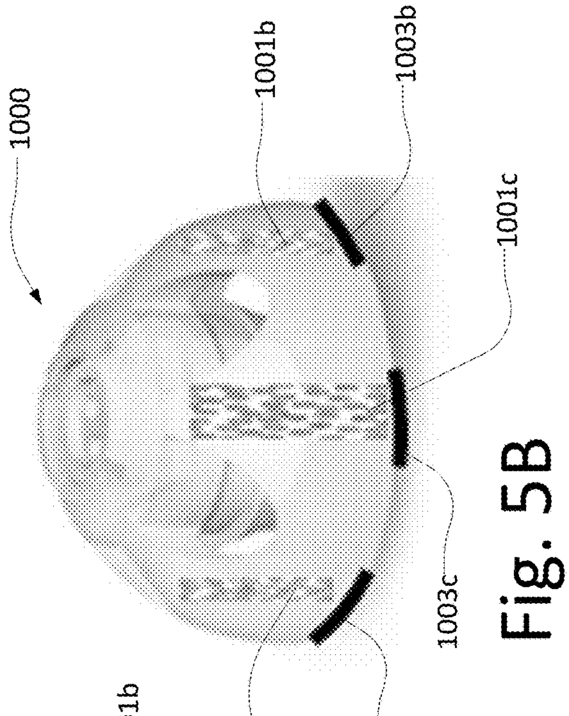
FIG. 5B illustrates an example of a dome of a hearing aid comprising sensors integrated into the dome material.
Figure 5A:
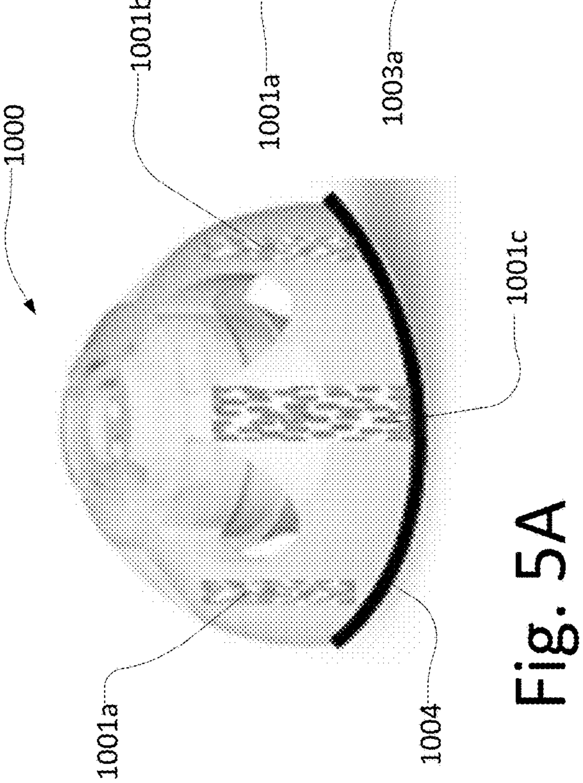
FIG. 5A illustrates a dome of a hearing aid comprising sensors integrated into the dome material.

Thus, to open the possibility of using non-custom made domes with electrodes therein, it is proposed to make a soft gel-based dome which is configured with conductive particles. That is, the gel dome would be constructed with an oxide material that would act as a flexible-dry contact electrode which could be used to record bioelectric signals from the ear. The particles could be deposed in the gel material on a uniform distribution to create a single recording electrode or in separate deposition clusters to create multiple recording sites. The suggested constructions are illustrated in more detail in FIG. 5A and FIG. 5B, where a dome 1000 is illustrated. In an example embodiment, the dome 1000 comprises a plurality of metal oxide particle pockets 1001*a*, 1001*b*, 1001*c*, each having oxide metal particles therein to create a dry-contact electrode in the hearing aid dome configured to especially record EEG signals. As illustrated in FIG. 5A, in one example the particle pockets may be in communicative contact with a single collector 1004 thereby creating a single electrode with three contact points via the three particle pockets. In another embodiment illustrated in FIG. 5B, the dome 1001 is configured as multiple electrodes, since each of the particle pockets 1001*a*, 1001*b*, 1001*c* is connected to separate collectors 1003*a*, 1003*b*, 1003*c*, thereby creating three separate electrodes forming an integrated part of the dome.

Figure 5C:
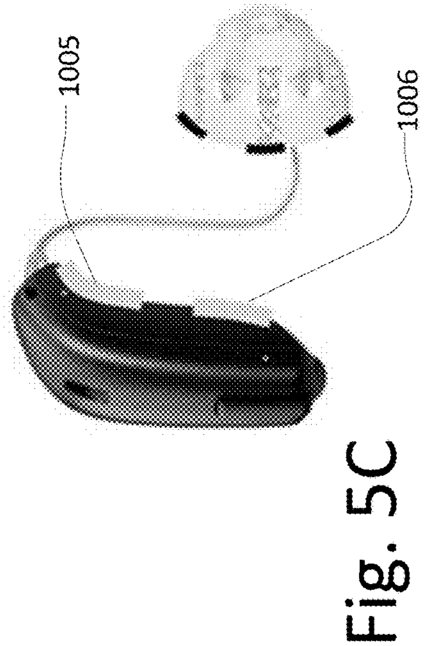
FIG. 5C illustrates the dome of FIG. 5A when mounted to a RITE style hearing aid with a behind the ear part comprising sensor configurations.

To maximize the recording sensitivity of the system, the hearing aid is in one example configured with a ground electrode 1006 and a reference electrode 1005 as illustrated in FIG. 5C. As illustrated in the Figure, the ground electrode 1006 and the reference electrode 1005 are configured to be placed in the shell/behind the ear housing of the hearing aid. It should be noted that the material of the gel dome/particles affects the impedance of the electrodes. Also, the shape of the electrodes in the gel dome matters. Ideally the area of the electrodes should be maximized to create a larger collection surface of the electrodes. Further, the signal captured by the proposed electrodes would need to be amplified.

There are pros and cons in view of incorporating sensors in either standard hearing aid domes or custom made domes, but both possibilities exist and both examples are presented in this disclosure. Incorporating sensors into a standard dome as just described provides the possibility to create a "works for all" solution, whereas a custom made solution will be optimized for the specific hearing aid user. Therefore, it has also been considered how to incorporate sensors in a custom style hearing aid, where the dome is custom made to the user (to be explained in further embodiments).

Figure 6A:
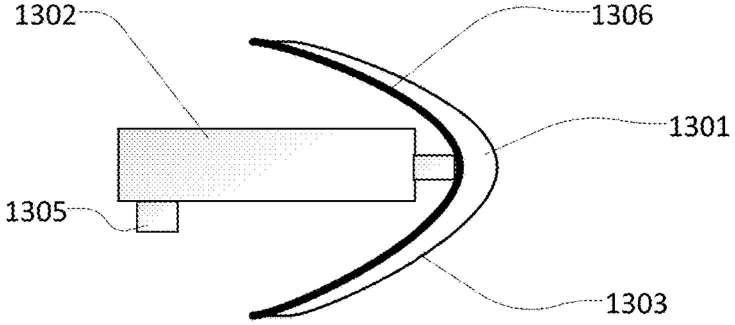
FIG. 6A illustrates an example of a dome of a hearing aid connected to a receiver of a RITE style hearing aid, where the dome comprises at least part of a sensor.
Figure 6B:
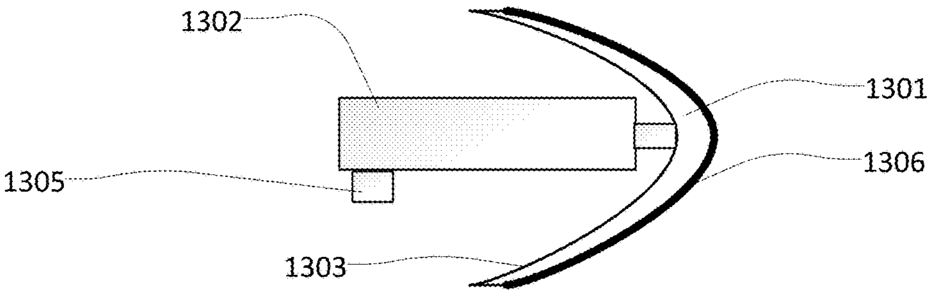
FIG. 6B illustrates an example of a dome of a hearing aid connected to a receiver of a RITE style hearing aid, where the dome comprises at least part of a sensor.
Figure 6C:
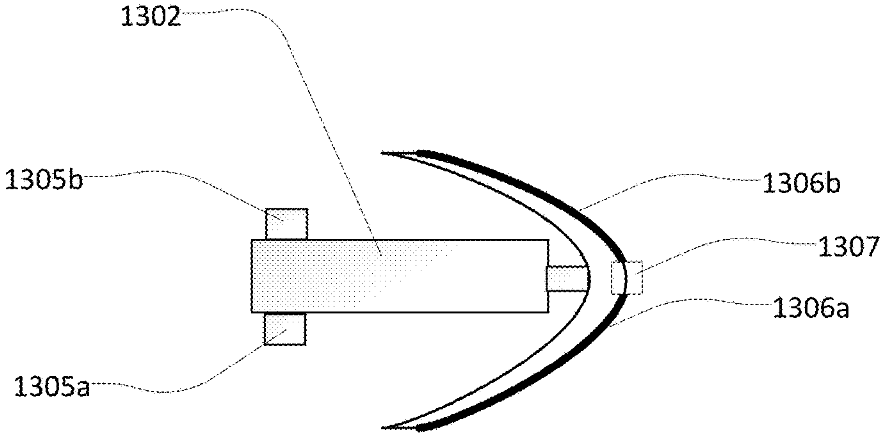
FIG. 6C illustrates an example of a dome of a hearing aid connected to a receiver of a RITE style hearing aid, where the dome comprises at least part of a sensor and a wax filter is included.

That said, another standard dome solution which also incorporates a sensor type into the dome is illustrated in FIG. 6A, FIG. 6B and FIG. 6C. Here, at least a part of the speaker unit configuration and a least a part of the dome comprises one or more sensor parts of the one or more sensors, wherein the speaker unit configuration at least comprises a printed circuit board for providing electrical communication for the data recorded by the one or more sensors. Accordingly, in this embodiment illustrated, the dome is more specifically configured with a PPG type sensor, but where the photo detector, generally forming part of the PPG sensor is integrated into parts of the dome of the hearing aid. By having a PPG sensor, or at least parts thereof integrated into the dome of the hearing aid, the sensor would take up less space in e.g. a speaker unit in for example a RITE hearing aid style.

Thus, in an embodiment illustrated in FIG. 6A, a hearing aid dome 1301 of a hearing aid is illustrated in connection with a speaker unit 1302 of the hearing aid. The dome 1301 is in the embodiment illustrated made photo sensitive. That is, the dome 1301 is configured with a photo sensitive material dome 1306, in this case on the inner side of the dome 1301 facing the speaker unit 1302. The photo sensitive material could be printed directly onto a dome or printed onto a flat material and then transferred onto the dome. As illustrated in FIG. 6A, the solution thus in one embodiment comprises a photo sensitive material 1306 placed on the inside of the dome 1301. In this configuration the sensitive area faces outwards, making the light having to pass through the dome 1301, where the dome 1301 is substantially transparent 1303 allowing light to pass to enter the tissue of the skin. As seen in FIG. 13A, the Light emission is directed from an LED 1305, in this example arranged in connection with the speaker unit. Thus, the emission of light is directed from a part of the speaker unit, whereas the detection of light, in contrast to the examples the described in relation to FIGS. 3A, 3B and 3C, is happening within the dome 1301. Thus, the LED 1305 and the photo detector 1306 of the PPG sensor does not in this embodiment need to share the same sensor PCB.

Another suggested solution is to mount the detector on the 'inside' of the dome. This way the detector is protected by the dome material and ensures robustness, comfort and biocompatibility. Utilizing this approach, it would also be possible to mount a traditional discrete photo detector in a dome. In any of the suggested cases, it is suggested that the dome is transparent to the wavelengths emitted by the transmitter, thereby allowing the PPG sensor to emit light onto the skin of the ear.

In another example illustrated in FIG. 6B, the photo sensitive material 1306 is configured to be arranged on the outside of the dome 1301. This creates a closer skin contact providing an optimized performance. Also, in this embodiment the LED light emitter 1305 is configured to be arranged in connection with the speaker unit 1302.

In a further embodiment illustrated in FIG. 6C, it is suggested that the photo sensitive detector (i.e. the photo sensitive material 1306) is split into two areas 1306*a*, 1306*b*, where the two areas are split by for example a wax filter 1307. In this embodiment, the solution is configured with two LED emitters 1305*a*, 1305*b* connected to the speaker unit 1302 to ensure that the two photosensitive areas 1306*a*, 1306*b* is within the focus area of the LED emitters.

In general, by providing a photo sensitive material integrated into parts of the dome or the speaker (as previously described), the photosensitive areas is increased, the sensitivity is increased lowering the system current consumption, the fit rate is increased, more free space for other components within the speaker unit is achieved, a reduction in motion artifacts and improved signal quality.

Another possible solution of integrating sensors into the dome is to utilize carbon nanotubes (or materials with similar properties), which is integrated onto the domes by e.g. printing technologies. In general, carbon nanotubes (CNT) can be made with different properties making them suitable for e.g. EEG electrodes, photo detectors and temperature dependent properties. This mean that using carbon nanotube integrated into the dome different kind of sensors of the dome can be created. They are thus very versatile materials and it may even be possible for one carbon nanotube sensor to have multiple functions such as both EEG and temperature sensing, when ensuring that the controlling logic is constructed so as to allow a switch between e.g. resistance measurement, voltage measurement and current measurement. In general, it is suggested to attach the carbon nanotube to the dome material by methods such as ink jet printers or coating. If coated onto a flexible material such as a hearing aid dome the sensor itself is flexible. The coating is often in the range of nanometers to a few hundred micrometers thick making it take up very little space.

If placed onto the dome it is ensured that the carbon nanotubes create a good skin contact as the 'spring tension' from the dome is used to secure the speaker unit inside the ear, by pushing against the ear canal. As discussed above this is advantageous for most biosensors. Thus, using carbon nanotubes to realize sensors solves the two main issues: size and contact robustness. These two factors are what makes it more attractive over previously known solutions as discrete silicon based components take up more space, will not provide constant robust skin contact while the soft flexible carbon nanotubes will likely also increase comfort especially of EEG electrodes. Furthermore, the choice of CNT or similar materials printed on the dome allow the creation of multiple electrodes. This brings the advantage of being able to choose one or several electrodes with best contact and signal quality thus making it easier to hit the 'EEG sweet-spot' in the ear canal compared to the conventional placing of the electrodes. The signal acquisition circuit could also dynamically alternate between the instances to select the best option provided by multiple electrodes. This improves ease of use as the user or health care professional does not need to take care in positioning/twisting the dome correctly inside the ear. Another option (also to save number of required contact points) is to connect some of the 'arms' in parallel, thereby averaging the signal providing higher SNR (could also be done in signal processing).

Given domes are disposable or replaceable, an interface to the speaker unit must exist (described in an example in the disclosure).

Accordingly, as illustrated in e.g. FIG. 8 and FIGS. 5A, 5B and 5C, the illustrated sensors could be implemented as carbon nano tubes as just described. Also FIGS. 6A, 6B and 6C illustrates dome sensor solutions where the sensors material could be made as a carbon nanotube.

Custom Mold Dome

As mentioned, a custom made type dome may also be configured with one or more sensors to record one or more different biometrical signals in the ear canal of a user of a hearing aid. The pros of using a custom mold vs. a standard mold or even a dome includes:

- Placement repeatability: Same measurement location from time to time as a custom mold will only fit 1 specific way in the ear canal. The signal will be consistent from insert to insert, which (likely) simplifies signal interpretation.
- Skin contact: The closer skin contact of a custom mold, the more controlled the optical path in the ear will be. Close skin contact results in higher AC signal in the data, which corresponds to heartbeat. Further close skin contact results in higher AC to DC ratio, which enables larger resolution of the AC signal, and close skin contact leads to overall higher signal strength and thereby better resolution.
- Movement artefacts: Lower movement due to 'perfect' ear fit, i.e. no room to move. The consistent optical path, from constant skin contact, yields fewer non-pulsatile tissue noise i.e. higher SNR.
- Ambient light shielding and controlled optical path: The non-transparent face-plate in custom molds also shields the sensor from external ambient light which degrades SNR e.g. through changes in light when running (sun shining through the leaves/trees in a forest), driving (sun behind trees), changing ambient light (e.g. television when watching movies) or any other case where ambient light will vary. The light shielding also removes static ambient light causing a DC offset in the signal thereby deteriorating the SpO2 and other measures. It can also saturate the sensor making all measures impossible, or if adaptive gain is used reduce signal amplitude/resolution. The custom mold will act as an optical barrier between LED and sensor. The otherwise occurring 'light bleed' will have similar effects as ambient light both in an AC and DC nature and can not be compensated for through traditional means of ambient light cancellation. Therefore, this will have a profound improving effect on signal quality.

The custom made mold contains essentially a flexible PCB to which all of the sensors is connected. The sensor, LEDs and other devices could be placed either on flex 'arms' enabling a high degree of freedom in regards to placement. Similarly, litz wires may substitute the arms. This enables the consistent placement of sensors in molds for a wide variety different of ears. The remaining part of the electronics required for PPG and processing (if not all contained in ear), may be placed behind ear, in a RITE type of implementation. Potentially, having a companion device for data display, processing, settings or similar. An example of such a device is a smartphone with a companion app.

Thus, according to an embodiment, the in-the-ear part may be configured as a custom mold, wherein the receiver is arranged within the custom mold in close arrangement with the one or more sensors, wherein a printed circuit board (PCB) is wrapped around a protrusion extending from a cover plate of the custom mold, and wherein the PCB is configured to comprise at least one or more sensors.

Figures 7A, 7B:
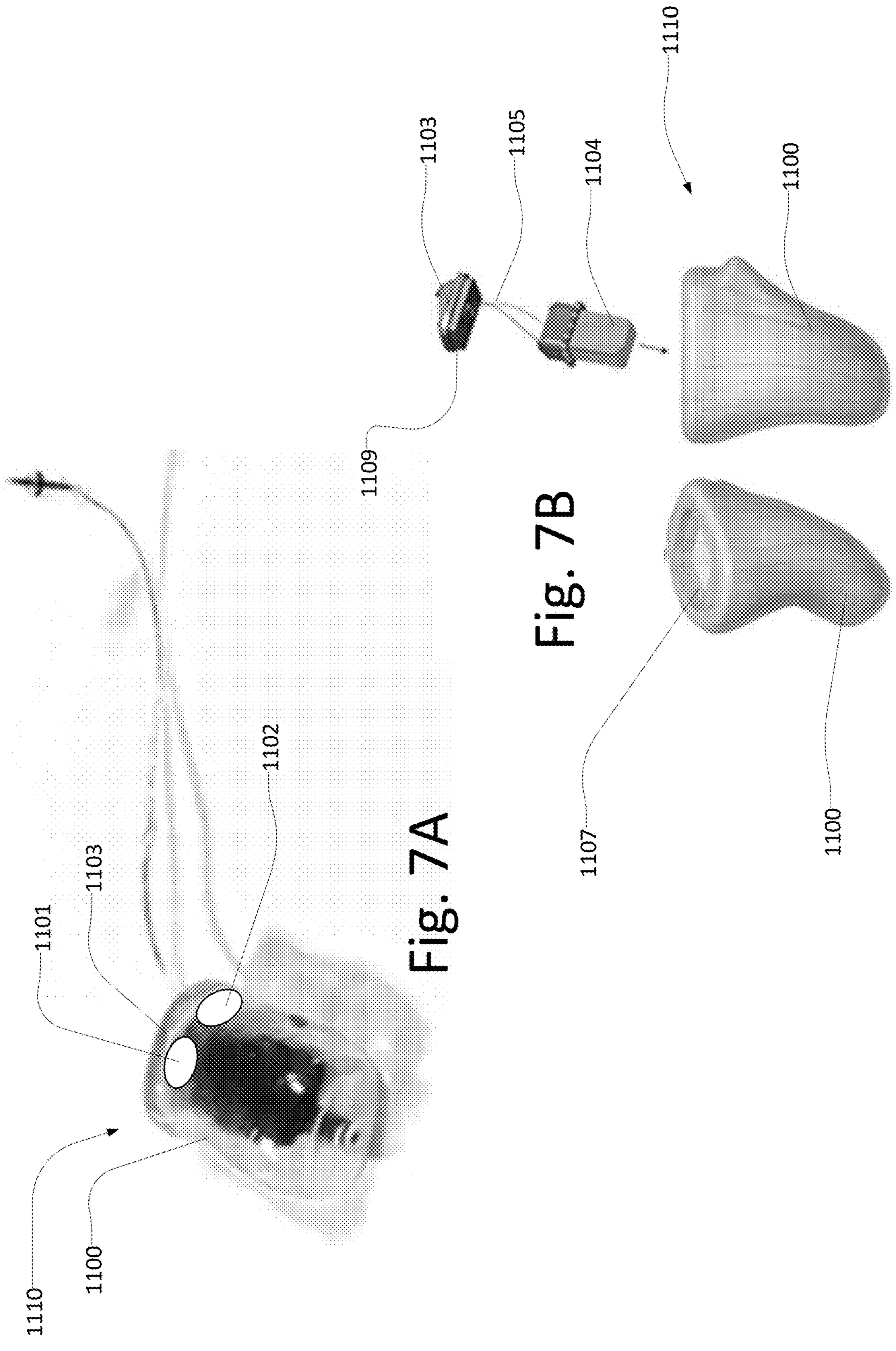
FIG. 7A illustrates a custom made style hearing aid with sensors in the custom mold.
FIG. 7B illustrates a custom made style hearing aid with sensors in the custom mold in an exploded view.

In more detail a custom mold may be configured as described in the following. A general schematic example of a custom mold 1110 is illustrated in FIG. 7A, where sensors 1101, 1102 are placed on the custom mold. The arrangement of the sensors in a custom mold is described in the following in different examples as suggested in this part of the disclosure. The following will mainly focus on PPG sensors for use in custom molds, but other sensors could be contemplated.

To obtain robust PPG data in a hearing instrument setting several different ways of integrating a PPG sensor into a custom ear mould is propsed. All presented solutions in the following are based on a multi-emitter (LED/LASER) multi-detector (photo detector) setup with controlling circuits and potential additional components (e.g. other sensors like an accelerometer, capacitors or others). However, even though several emitters and detectors are described in the following it should be noted that a setup utilizing only one emitter and one detector can be contemplated. In the following description, it should be noted that the shell material 1100 preferably is made from a transparent material, which especially allows light to pass in order to record the PPG signals from the detector.

Illustrated in FIG. 7A is as mentioned a general custom mold 1110 shown. The custom mold 1110 comprises a faceplate 1103 which is configured with a plurality of the electrical components of the hearing aid. FIG. 7B illustrates an example of an exploded view of a custom mold similar to FIG. 7A, where it is seen that the custom mold comprises a receiver 1104 connected via electrical wires 1105 to a cover plate 1103 (also denoted a face plate throughout the disclosure). The custom mold 1110 is configured as a 3D printed shell based on an ear impression of a customer to which the hearing aid should be fitted. The shell of the custom mold (i.e. the custom mold) comprises a cutout 1107 where a cover 1109 holding the receiver cable is configured to be inserted into, by for example using an adhesive. To implement sensors into the custom mold solution, several possibilities is considered in the following.

Figure 7C:
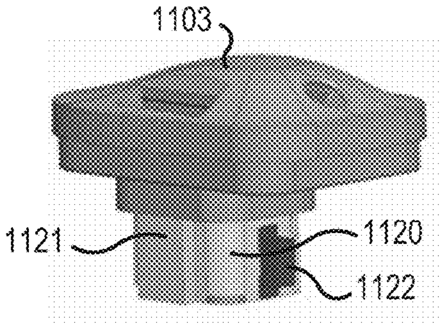
FIG. 7C illustrates a cover plate of a custom mold with sensors arranged in connection thereto.
Figure 7D:
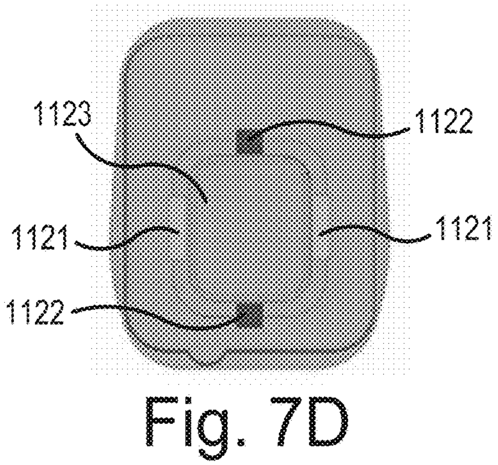
FIG. 7D illustrates a bottom view of the cover plate of FIG. 7C.

Further, the custom mold may be configured with an inner core of the cover plate, wherein the inner core is configured as a hollow interior enabling placement of controlling components, e.g. sensor front-end or other sensors, such as accelerometer, and miscellaneous components (for e.g. capacitors) on the inside thereof. Accordingly, as illustrated in FIG. 7C, a cover plate 1103 configured to be connected to a flexible PCB 1120 construction forms part of the custom mold. The PCB 1120 is wrapped around a protrusion extending from the cover plate 1103, and the PCB 1120 is configured to comprise at least one sensor, such as an LED emitter 1122 and a detector 1121. As illustrated in FIG. 7D the inner core 1123 of the cover plate may be hollow enabling placement of controlling components, e.g. sensor front-end or other sensors, such as accelerometer, and miscellaneous components (for e.g. capacitors) on the inside. The components of the hollow inner side of the inner core 1123 may contain sensors or other electrical components connected to the same PCB as the LED emitter and the detector. In this way the whole volume of the cover plate is effectively utilized while the thickness of the cover plate is kept as small as possible to improve fit rate of customers.

Figure 7E:
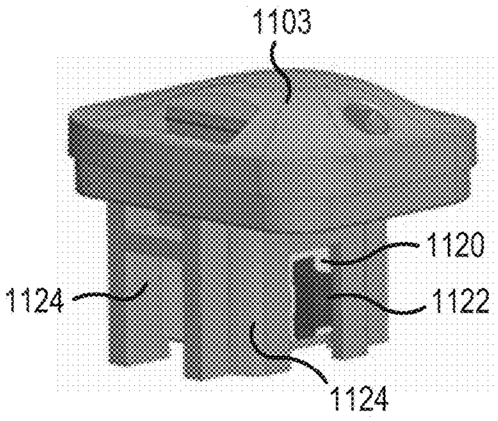
FIG. 7E illustrates an example of a cover plate having sensors arranged in connection thereto.
Figure 7F:
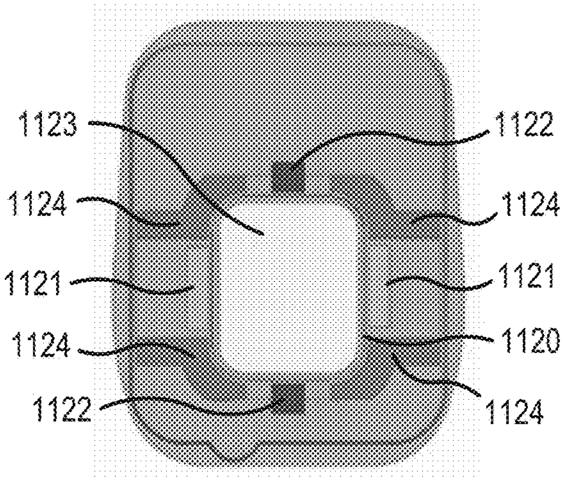
FIG. 7F illustrates a bottom view of the cover plate of FIG. 7E.

When especially using PPG sensors utilizing LED emitter and detectors as described throughout the disclosure, it is relevant to consider how to avoid light from the LED emitter hitting directly at the photodetector prior to entering any tissue and causing a noise component in the recorded PPG signal. Thus, when considering the presented solutions for custom molds described herein, avoidance of this type of noise component is obtained by providing light blocking features within the cover plate. Accordingly, a plurality of light blocking elements may be arranged at each corner of the cover plate enabling a blocking of direct light transmission between sensor parts. As illustrated in 7E and FIG. 7F, a cover plate 1103 similar to FIGS. 7C, 7D is illustrated. The cover plate 1103 comprises, in addition to the features already described in relation to the previous FIGS. 7C and 7D, a plurality of light blocking elements 1124 arranged at each corner of the cover plate. The light blocking elements 1124 in this way is configured to block the potential light path between the detector 1121 and the LED emitter 1122, which are as seen in the Figures arranged on perpendicular sides of the PCB 1120. The light blocking elements 1124 may protrude from the cover plate as the flex PCB is wrapped around the core as shown in FIG. 7C and FIG. 7E. The light blocking elements 124, may also be used to insert the PCB into the cover plate. This makes the assembly easier or could be used as snap feature to hold the PCB in place.

Figure 7I:
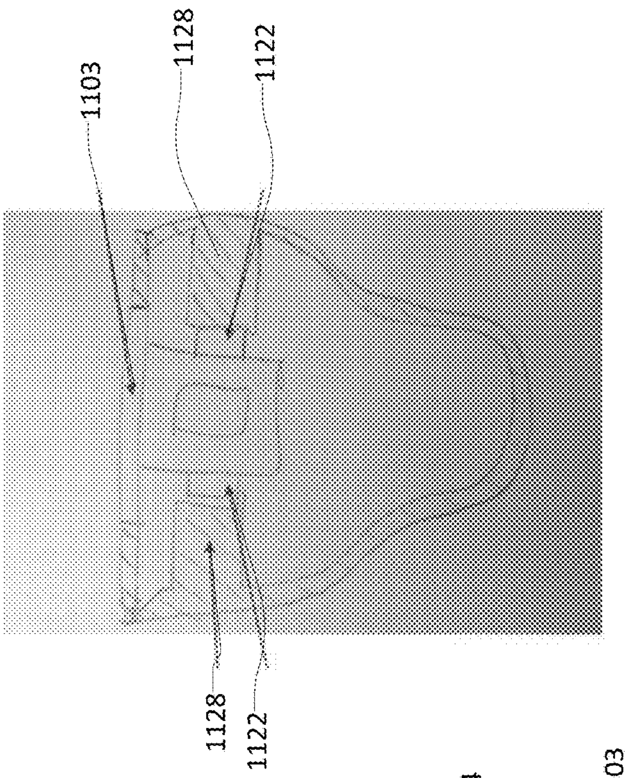
FIG. 7I illustrates a cross-sectional view of a custom mold with sensors arranged therein.
Figure 7G:
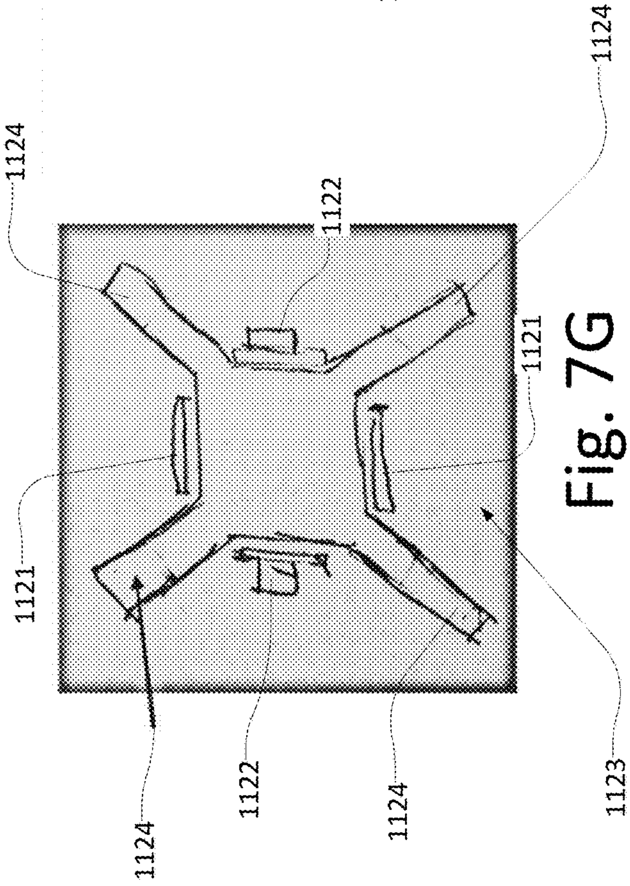
FIG. 7G illustrates an example of a cover plate with sensors.

In another example illustrated in a sketch in FIG. 7G, the light blocking elements 124 is integrated into the inner core 1123. In this way, the light blocking elements 124 is protruding out from the inner core 1123 so as to ensure that the potential light path between the LED emitter 1122 and the detector 1121 is blocked.

Figure 7H:
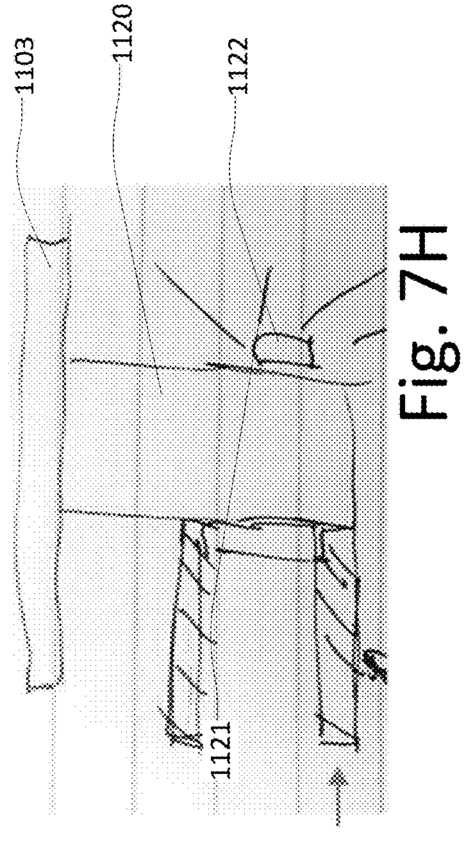
FIG. 7H illustrates a side view of an example of a cover plate with sensors.

Another possible solution to ensure that the detector is not influenced by direct light from the LED emitter is illustrated in a sketch in FIG. 7H. Here the cover plate 1103 is configured with a protrusion comprising the PCB 1120 onto which a light emitter 1122 and a detector 1121 is arranged. Further, in this solution, the detector is surrounded by a substantially rigid tube made from a flexible polymer ensuring that the tube is blocking all light coming from an angle into the detector, and thereby protecting the detector from any noise signals.

As illustrated in FIG. 7I, the custom mold may also be configured with light guides as an alternative, or supplement, to the previous presented solutions. That is, in FIG. 7I, a custom mold is illustrated wherein the cover plate 1103 is configured with the previously described protrusion with a PCB to which the LED emitter 1121 and the detector (not illustrated) is attached. In this example, the LED emitter is configured to be in contact with a light guide 1128, which ensures that emitted light from the LED emitter 1122 is transmitted to the outside of the shell of the custom mold, without reflections inside the shell. These light guides 1128 may be 3D printed in the same material together with the shell.

As described in previous embodiments of the custom mold solutions, the PCB may form a protrusion of the cover plate. That is, the cover plate may be configured with a PCB extending therefrom. The construction thereof can be formed in some exemplary ways explained in the following, where generally the electrical components and sensors are placed on a PCB module, wherein the PCB module is arranged in the faceplate of the custom shell so as to protrude therefrom into the custom mold. The placement of the electrical components on a PCB module allows to use a generic PCB for different faceplate sizes, that are used for custom molds of different fitting levels. This way less parts have to be produced and assembly is simplified. The height of the PCB is thereby relevant, since it adds to the lengths of the custom mold. A longer custom mold is possibly more visible and therefore less discreet. The presented solutions minimize the height of the PCB, and comprises a PCB of the custom mold, which is configured with a bended portion so as to comprise an inner side and an outer side, wherein each of the outer sides of the PCB comprises at least one sensor configuration such as one LED emitter and one detector, and wherein the PCB is configured to be connected to the cover plate via an insertion area of the cover plate and insertion areas of the PCB.

Figure 7J:
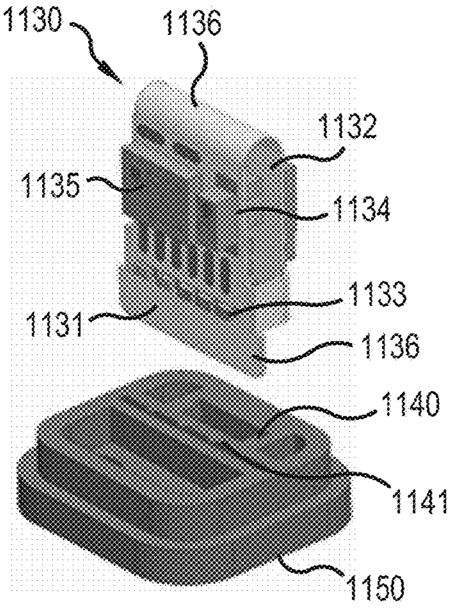
FIG. 7J illustrates a cover plate of a custom mold, where a PCB connecting with the cover plate and having electrical components and sensors arranged thereon is shown form a first side.
Figure 7K:
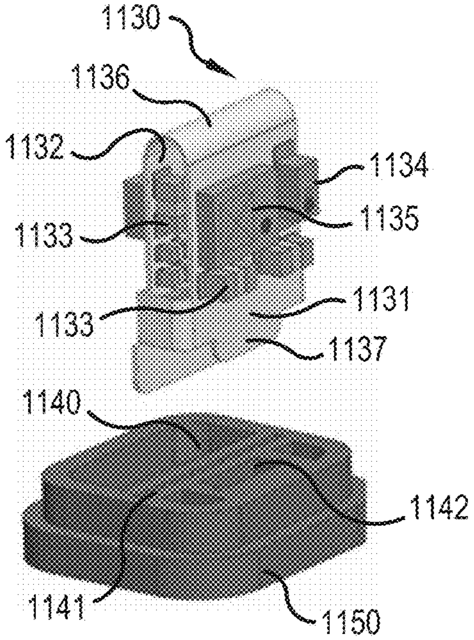
FIG. 7K illustrates the cover plate of FIG. 7J where the PCB is seen from a second side.

Accordingly, FIG. 7J and FIG. 7K illustrates two different views of a flexible PCB 1130, which is bended so as to comprise an inner side 1132 and an outer side 1131. As illustrated different electrical components 1133 are arranged onto the PCB on both the inner side 1132 and the outer side 1131 of the PCB construction. The PCB is in an end facing away from a cover plate insertion area 1140 configured with a bended area 1136 from which two sides of the PCB extend to form the outer sides of the PCB. On each of the outer sides 1131 of the PCB at least one LED emitter 1134 and one detector 1135 is arranged as seen in FIG. 7J and FIG. 7K. Furthermore, as already described a plurality of electrical components 1133 is arranged on both of the two outer sides 1131 of the PCB. In addition, and as best illustrated in FIG. 7K, also the inner sides 1132 is configured to have electrical components 1133 arranged on the PCB. This optimizes the area at which electrical components can be arranged at PCB within a custom mold hearing aid.

The flexible PCB 1130 is configured to be connected to the cover plate 1150 via an insertion area 1140 of the cover plate 1150. That is, as illustrated in FIG. 7J and FIG. 7K, the PCB is configured with two insertion areas 1136, 1137 formed on each of the two outer sides 1131 of the PCB in the end facing the cover plate 1150. As can be seen in FIG. 7J as first insertion area 1136 is configured to inserted into a similar shaped groove 1141 in the cover plate 1150, whereas a second insertion area 1137 illustrated best in FIG. 7K, is configured to be inserted to a second groove 1142 in the cover plate 1150. In this way it is ensured that the PCB can easily be fitted into the cover plate independent from the general shape of the custom mold. Thus, such standard PCB with electrical components and sensors can be used for a plurality of user fitted custom molds. In a preferred embodiment, the PCB is attached to the cover plate by pushing the PCB into the insertion area and using an adhesive or similar material to fasten the PCB within the cover plate. This also accounts for the following described embodiments.

Figure 7M:
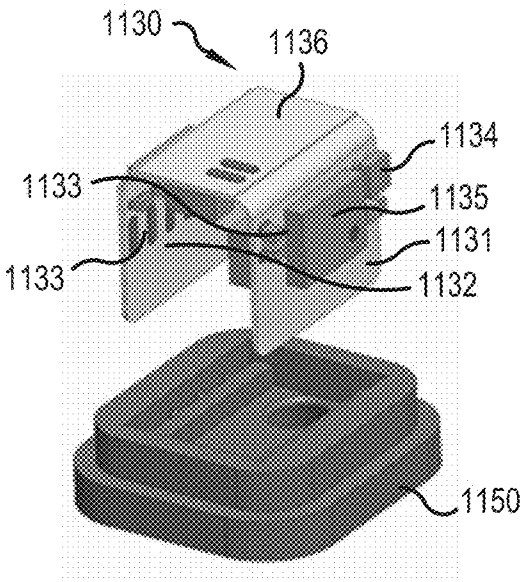
FIG. 7M illustrates an example of a cover plate of a custom mold, where a PCB connecting with the cover plate and having electrical components and sensors arranged thereon is shown form a first side.
Figure 7N:
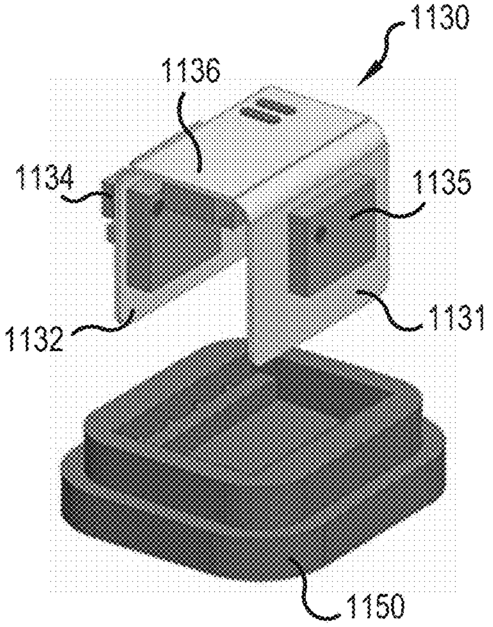
FIG. 7N illustrates the cover plate of FIG. 7M where the PCB is seen from a second side.

A similar solution is illustrated in FIG. 7M and FIG. 7N. Here the PCB is configured with a larger bend area 1136 than in the previous described FIG. 7J and FIG. 7K. Thus, the main difference is that the height of the PCB is decreased while increasing the width of the PCB. The PCB comprises as previously described a bended area 1136 from which two sides of the PCB extend to form the outer sides 1131 of the PCB. On each of the outer sides 1131 of the PCB at least one LED emitter 1134 and one detector 1135 is arranged as seen in FIG. 7M and FIG. 7N. Furthermore, as already described a plurality of electrical components 1133 is arranged on both of the two outer sides 1131 of the PCB. Also this solution is configured to be pushed into the cover plate 1150 and fastened thereto by e.g. an adhesive material, as previously described.

Figure 7O:
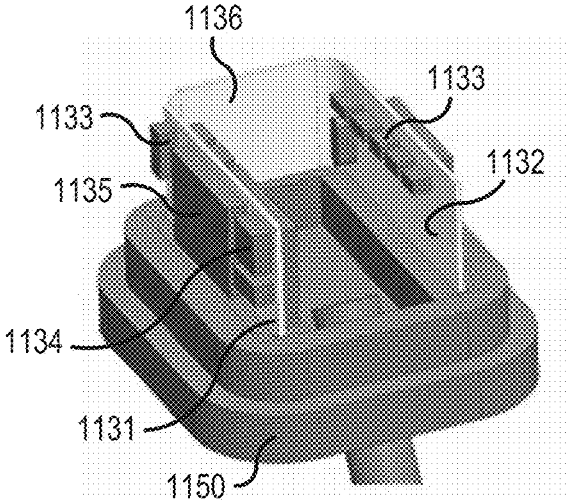
FIG. 7O illustrates an example of a cover plate of a custom mold, where a PCB connecting with the cover plate and having electrical components and sensors arranged thereon is shown form a first side.
Figure 7P:
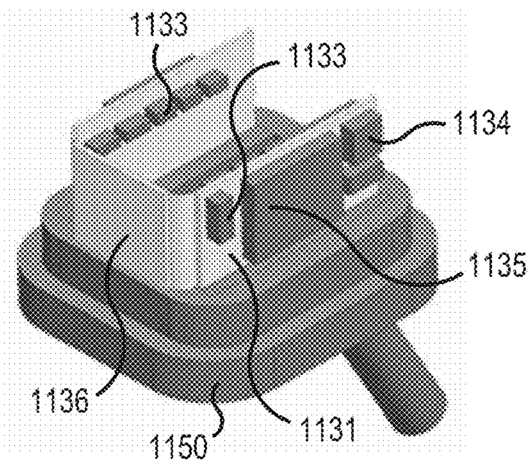
FIG. 7P illustrates the cover plate of FIG. 7O where the PCB is seen from a second side.

In FIG. 7O and FIG. 7P, another similar solution as the previous described is illustrated. As can be seen, in this solution, the PCB is also configured with a bended area 1136, but arranged to be placed in the cover plate 1150 with the bended area contacting a part of the cover plate 1150. That is, each of the two outer sides 1131, and the bended area 1136 (basically all of the edges of one side of the PCB) is in contact with the cover plate 1150. This results in an even further decrease in the height of the PCB as compared to the previous described solutions. The remaining features as previously described is the same and will not be explained again, but reference is made to the figures and the numbering previously described. The overall shape of the PCB is here generally U-like shaped.

Figure 7Q:
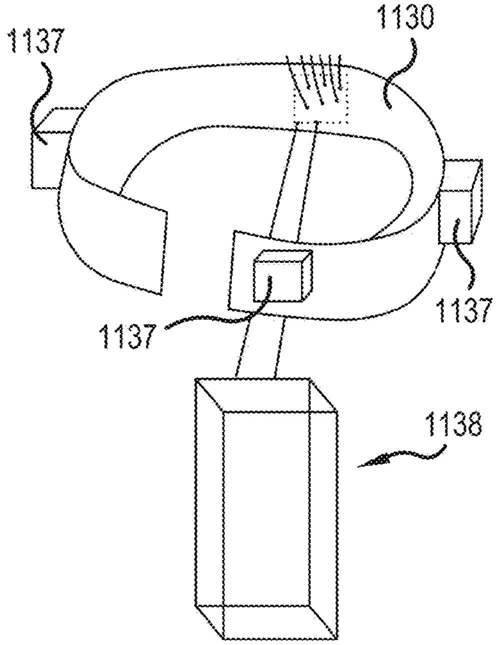
FIG. 7Q illustrates a PCB of a customed mold formed as a ring-shaped flexible PCB.

In FIG. 7Q it is illustrated how the PCB may be formed as a ring-shaped flexible PCB 1130. Here the LED emitter(s) and the photo detector(s) forming the PPG sensor 1137 are arranged on a ring-shaped flexible PCB 1130, which is made from a flat flexible PCB. By forming the PCB into a ring shape, the PCB gets pretensioned. The PCB gets affixed by pushing it into the custom shell. Due to the spring force of the PCB, the PCB will expand and push the LED emitter(s) and photodetector(s) onto the shells inner surface. This will ensure ideal light transmission properties through the shell and reduce skin reflection and direct light transmission. An option is to introduce grooves into the custom shell for placement of the PCB to ensure a firm connection between PCB and shell. This solution is independent of the receiver size, since the ring of the PCB is configured to expand according to the shell dimensions. Therefore, only one generic PCB is needed.

Figure 7R:
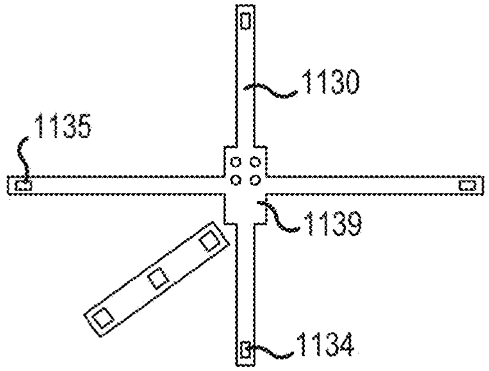
FIG. 7R illustrates a substantially star shaped PCB of a custom mold.

In FIG. 7R, a solution is illustrated, where the PCB 1130 is substantially star shaped and placed in the cover plate of the shell. This type of star shaped PCB 1130 is made from a flat flexible PCB, where the LEDs 1134 and photo detectors 1135 are placed at the ends of the "star". The center 1139 of this star is connected to the cover plate (not illustrated) and may contain more electrical components. By bending the arms and inserting the PCB into the custom shell, the LEDs and photo detector are again pressed to the inner surface of the shell as described before. Features in the shell may guide the 'arms' into the correct placement. They may be fixed into place by glue or other fixation material.

Speaker Connection with Dome

As indicated throughout the disclosure, several solutions exist on where to position the sensors in a hearing aid.

One possible solution is to integrate the sensors into the speaker unit as described in relation to FIGS. 4A, 4B and FIGS. 4C, 4D.

Another solution is to provide a dome of the hearing aid with sensors, as described in relation to FIGS. 5A, 5B, 5C and FIGS. 6A, 6B and 6C. Especially in the cases of the solutions where the dome comprises integrated sensors it is important that these sensors efficiently can communicate with the speaker unit to transfer information recorded by the sensors. That is, a PCB is normally not present in the dome, why any electrical communication with the remaining of the hearing aid needs to be via the speaker unit, where the electronic parts of the hearing aid in communication with other electronic parts of the hearing aid is located. Therefore, in sensor integrated domes, a solution for an efficient interface between the speaker unit and the dome is needed.

Figure 8:
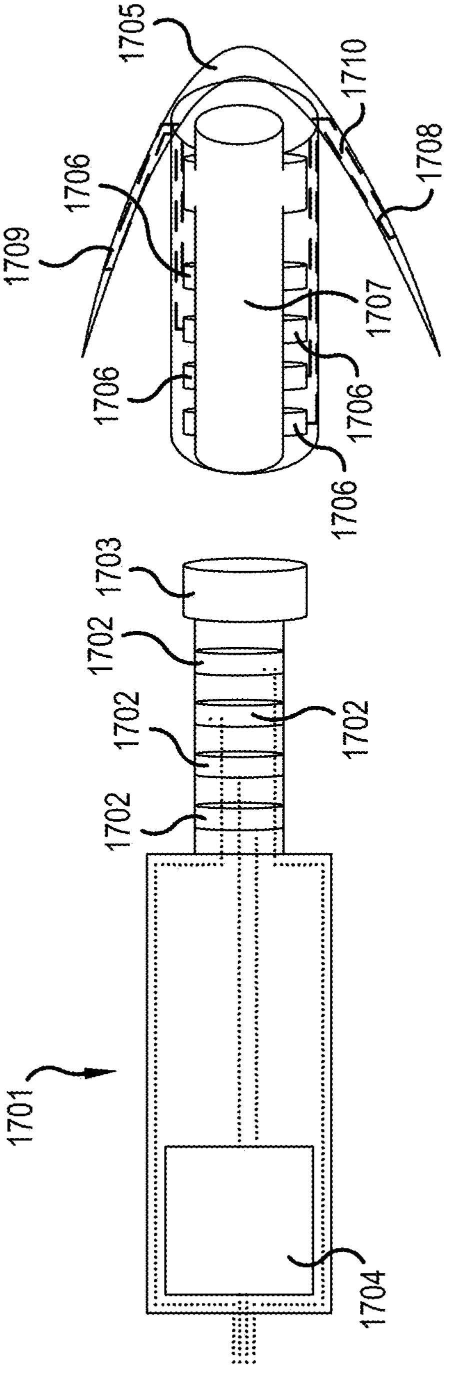
FIG. 8 illustrates a receiver unit connections with a dome having integrated sensors.

According to an embodiment, such interface is achieved by a speaker unit configuration configured with speaker unit sensor electronics and a plurality of electrical connections at an acoustical interface of the speaker unit configuration, and wherein the dome is configured with dome electrical connections and a dome acoustical interface so as to allow electrical communication between one or more sensor configurations of the dome and the speaker unit when the speaker unit acoustical interface and the dome acoustical interface connects. The solution of providing the speaker unit (i.e. speaker unit configuration) with an electrical interface, more specifically to provide the snout of the speaker unit with an electrical interface, is illustrated in FIG. 8 and will be described in further detail in the following. The described solution allows for users to swap out the domes without any knowledge about electronics i.e. exchanging domes will be identical to the current swap of domes. The solution will also allow for cheap electronics such as a NTC (resistive temperature sensor) or LED to be integrated into the dome, and disposed of, while the much more expensive driving/data collection circuit is integrated into the speaker unit and therefore not disposed of. Similarly, printed electronics such as printed temperature sensors or photosensitive materials will require an interface like this.

As illustrated in FIG. 8 the speaker unit 1701 is configured with speaker unit sensor electronics 1704 and a plurality of electrical connections 1702 within an acoustical interface 1703 of the speaker unit 1700. Similarly, the dome 1705 is configured with dome electrical connections 1706 and a dome acoustical interface 1707. Further the dome 1705 comprises at least one sensor, however two sensors 1708, 1709 is illustrated, which sensors 1708, 1709 is electrically connected to the electrical connections 1706 via an electrically conductive connection 1710 (illustrated with the broken line) integrated into the dome 1705. Thus, when the speaker unit 1701 is inserted into the dome 1705 via the acoustical interfaces 1703, 1707 of the speaker unit 1701 and the dome 1705 respectively, the electrical connections 1702 of the speaker unit 1701 and the electrical connections 1706 of the dome 1705 electrically engages and allows transfer of electrical information from the one or more sensors 1708, 1709 to the speaker unit sensor electronics 1704. In this way signal transfer from the sensors to the speaker unit is achieved while at the same time the dome is exchangeable.

As is apparent, the suggested solution according to FIG. 8 may of course include more or fewer electrical connections depending on requirements of the sensors included in the dome. The connections may transfer analog (e.g. electrical resistance or LED and photo detector currents) or digital (e.g. I2C, SPI or other communication) signals. The signals transferred from the dome to the speaker unit may be used/conditioned by electronics inside the ear and/or passed directly to the hearing instrument or electronics placed in between.

There are several ways to realize the described speaker unit-dome interface. One way of implementing the connection is to leverage the advantages provided by printed electronics. The electrical connections of the dome may be provided by printing electrically conductive traces onto the dome. They may be printed on a flat surface and then grafted onto the dome, which will result in nice synergies with printed sensors such as core body temperature sensors printed onto the dome which will provide much higher quality temperature readings as they will be less sensitive to the ambient environment. Similarly, photo detectors printed onto the dome will allow for a much higher sensitivity increasing signal quality. Another similar solution to the above could be to stick conductive film/foil (e.g. copper foil) to the dome realizing the electrical traces and connection, while another implementation could be to mold in conductive rings and wire connections into the dome material.

Sensors in Speaker Unit

Another solution, also described in relation to FIGS. 4A, 4B, 4C, 4D is to provide the sensors in the speaker unit in close proximity to the speaker unit. Several alternatives exist which will be explained in the following.

Figure 9:
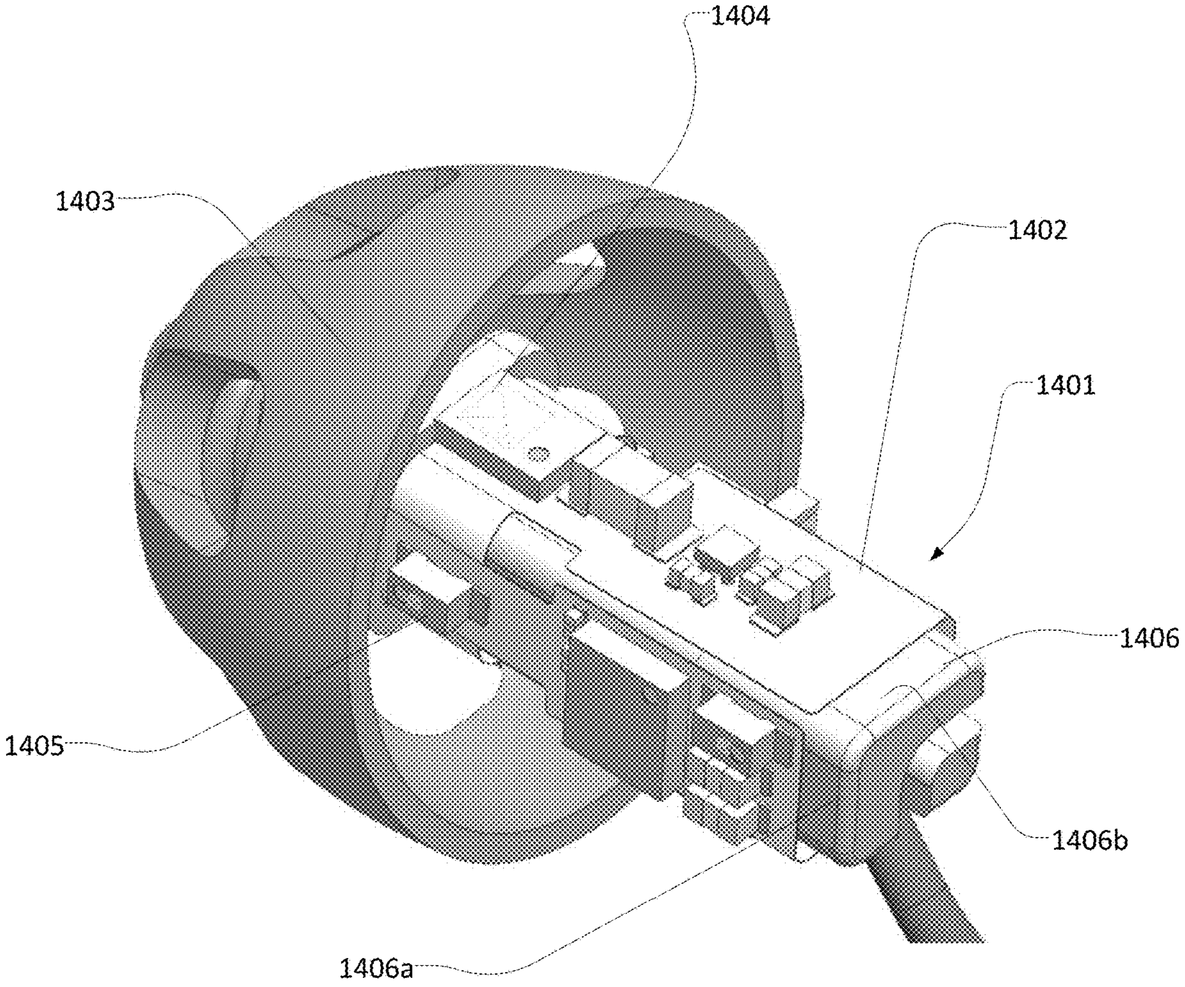
FIG. 9 illustrates a receiver unit comprising electrical components and sensors arranged on a PCB of the receiver unit.

A solution presented in FIG. 9 is to wrap a flexible printed circuit board 1402 around the receiver 1406. The flexible printed circuit board 1402 comprises at least one sensor, chosen as e.g. a PPG sensor having an LED emitter 1405 and photo detector 1404. As illustrated in FIG. 9, the PPG sensor is arranged on the flexible printed circuit board 1402 in a manner where the LED emitter 1405 is placed to emit light onto the inside of a dome 1403. That is, the LED emitter 1405 is arranged on a first side 1406*a* of the receiver 1406, whereas the photodetector 1404 is arranged on a second side 1406*b* side of the receiver 1406, wherein the first and the second side is substantially perpendicular to each other. In this way the full receiver area is utilized in addition to placing emitter and detector at an angle to each other, to reduce skin reflection. Another possible solution would be to arrange the LED emitter and the photo detector on the same side of the receiver, however potentially implementing the PPG sensor solution described in relation to FIGS. 3A, 3B, 3C. Such solutions would also avoid, or at least reduce, any noise in the recorded signals by the detector.

Figure 9A:
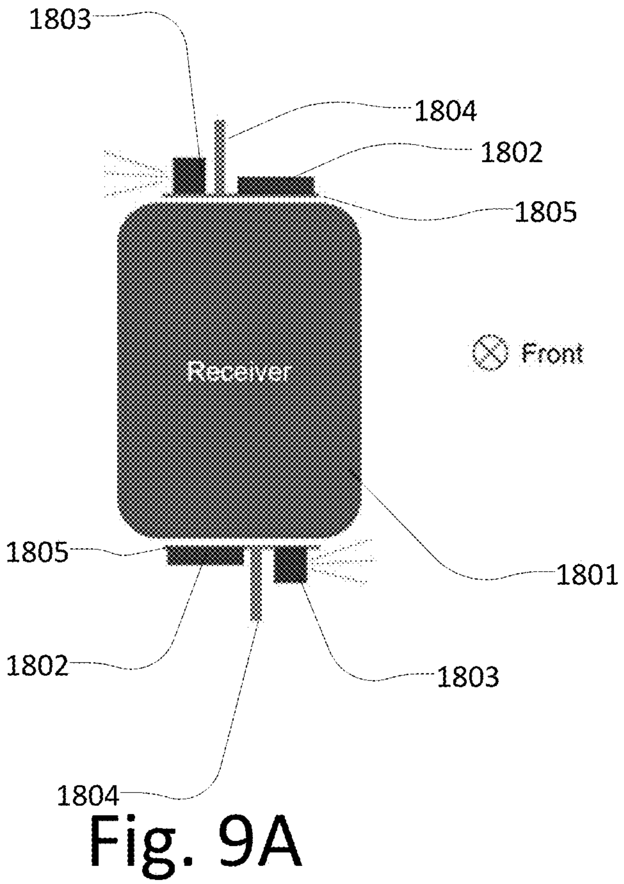
FIG. 9A illustrates an example arrangement of sensors in connection with a receiver of the type illustrated in FIG. 9.
Figure 9B:
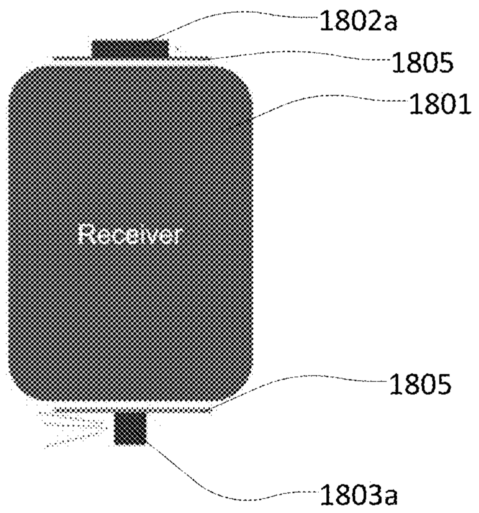
FIG. 9B illustrates an example arrangement of sensors in connection with a receiver of the type illustrated in FIG. 9.

Another possible solution, different from the flexible PCB formed around the receiver as just described, is to provide a substantially flat piece of PCB arranged on the top and/or bottom side of the receiver. This solution is illustrated in FIGS. 9A and 9B, where a receiver 1801 is illustrated as seen from the front. As can be seen the two sides of the receiver together forming the height of the receiver, when seen from the front, comprises in on case shown in FIG. 9A, a PCB 1805 in both the top and bottom of the receiver. Each of the PCB's 1805, comprises an LED emitter 1803 configured to emit light and a detector 1802 configured to record reflections from the tissue caused by the emitted light. As illustrated in FIG. 9A, the detector 1802 and the LED emitter 1803 is separated by a light blocker, so as to avoid a direct light path from the LED emitter to the photo detector.

In FIG. 9B, a similar solution is illustrated. However, in this case only one LED emitter 1803*a* and one detector 1802*a* is arranged in connection with a bottom and top, respectively, of the receiver 1801. Each of the LED emitter 1803*a* and the detector 1802*a* is arranged on a PCB 1805 as previously described.

Figure 9C:
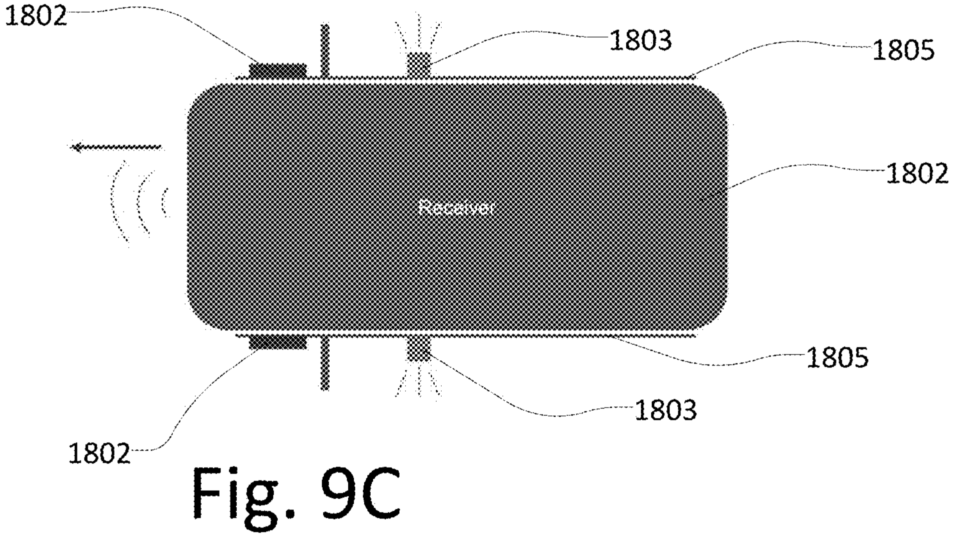
FIG. 9C illustrates an example arrangement of sensors in connection with a receiver of the type illustrated in FIG. 9.

In FIG. 9C as solution of a receiver 1802 comprising one or more sensors is illustrated. As can been seen in FIG. 9C, the receiver 1802 is seen with the front facing towards the arrow and the back of the receiver the opposite end. At two opposing sides of the receiver 1802 is arranged a sensor configuration similar to the one described in relation to FIG. 9A. As can be seen from FIG. 9C, the detector 1802 is arranged on the flat PCB 1805 together with the LED emitter 1803. Such configuration is arranged on two sides of the receiver 1802 as illustrated. The detector 1802 and the LED emitter 1803 is separated by a light blocker as previously described in relation to FIG. 9A.

Generally, the receiver of a RITE style hearing aid is configured with a speaker housing. When using sensors integrated onto the receiver via a PCB as described herein, it is relevant to consider the construction of the housing so as to allow the sensors to sufficiently and effectively transmit and receive the signals needed for recording of biometrical data. Therefore, the construction of the speaker housing containing the receiver and the electrical components thereof, including the sensors has also been considered.

In one example, the receiver housing (i.e. the speaker casing) is made from injection molded plastic assembled around the receiver and electronics, where the injection molded plastic comprises integrated light blocking features between LED and photo detector.

In an example, the receiver and the electronics could be over molded with transparent silicone, epoxy or other material. By using a transparent material like transparent epoxy, the PPG sensor components (i.e. the LED emitter and the detector) can be over molded and shine directly through the material. This ensures a compact design of the speaker unit.

Another example is provided by over molding with a light absorbing material. In this concept the receiver and electronics are over molded, while the LEDs and photodetectors are left free. The light absorbing material is acting as blocking feature between the sensor components.

Figure 9D:
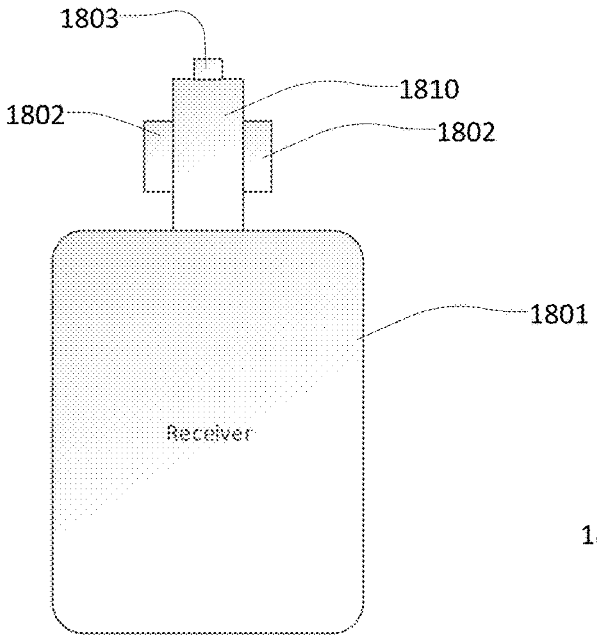
FIG. 9D illustrates an example arrangement of sensors in connection with a receiver of the type illustrated in FIG. 9.
Figure 9E:
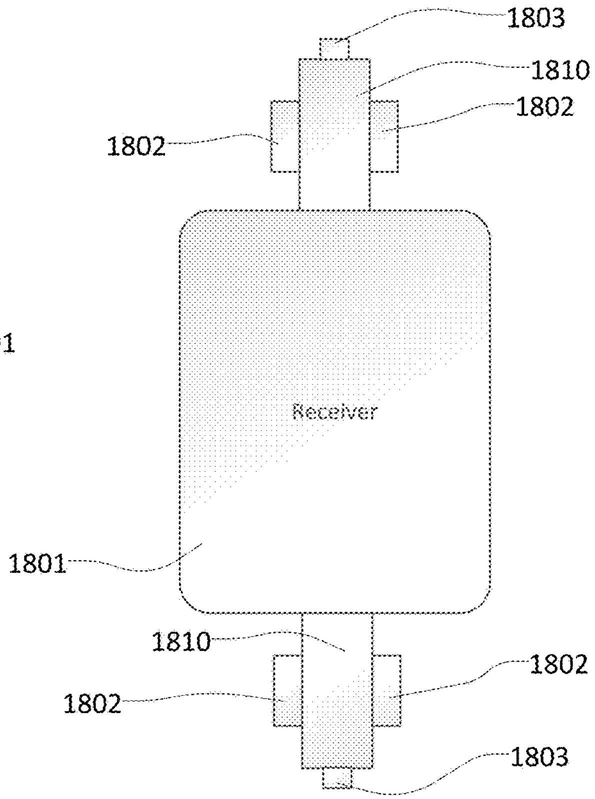
FIG. 9E illustrates an example arrangement of sensors in connection with a receiver of the type illustrated in FIG. 9.
Figure 9F:
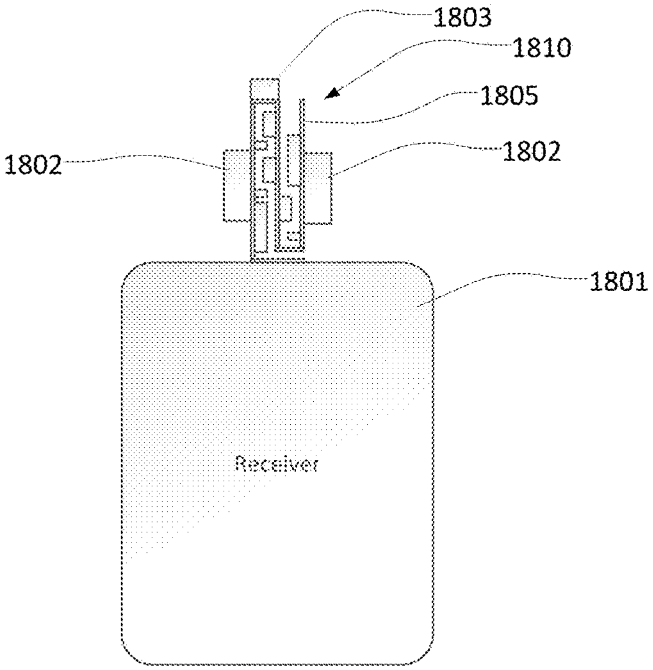
FIG. 9F illustrates an example arrangement of sensors in connection with a receiver of the type illustrated in FIG. 9.

In FIGS. 9D, 9E and 9F another solution is shown where the speaker unit (i.e. the housing containing the receive) is configured with a protrusion in at least one end thereof. The protrusion generally comprises the sensor components as illustrated and explained in the following for each of the Figures.

As can be seen in FIG. 9D, the protrusion 1810 may be arranged on the top of the speaker unit 1801. A flexible PCB (not illustrated) may be wrapped around the protrusion allowing for a high amount of PCB real-estate at a low receiver area. The solution also allow the optical components, such as the LED emitter 1803 and the detector 1802 to be placed at an angle to each other to reduce direct surface reflection, which would allow light to pass directly from the LED emitter 1803 to detector 1802 without entering the tissue (thereby not providing relevant signal). Furthermore, the construction places the optical components closer to the skin, which further decreases skin reflection and potentially increases signal quality due to more light entering the tissue (or at least at a more controlled location). The construction aims to utilize as much of the volume inside the ear as possible taking special consideration to the oval nature of the ear canal which allows for more build height having little room to increase in width without compromising fit-rate (significantly). The protrusion also allows for a LED emitter or detector to be placed facing inwards allowing for additional optical paths.

As can be seen in FIG. 9E, the protrusion 1810 may also be arranged on the bottom instead of the top of the speaker unit 1801. Alternatively, which is also forming part of FIG. 9E, a protrusion 1810 may be arranged on both the top and bottom of the speaker unit 1801. Having the protrusion 1810 in both the top and bottom creates a more symmetrical solution, which ensures a larger useable PCB area and freedom in component placement, while reducing skin reflection. This solution yields a more pronounced oval shape, which may fit more users than a single-side larger extrusion and conform better to the oval nature of the canal, thereby maximizing the ear canal volume utilization.

In FIG. 9F, an example is illustrated where the speaker unit 1801 comprises a protrusion part 1810, which is configured with a folded flexible PCB 1805, this to utilize the volume and stacking height available inside the ear while providing an optimized PCB component area (i.e. the area at which electrical components can be arranged on the PCB). The example of FIG. 9F utilizes the volume of the protrusion for placement of components, thereby allowing for much more electronics packed in the same volume. In addition to having the same advantages to the solutions described above. In terms of variations, the PCB may use combinations of the solutions described above e.g. using a protrusion for support or having parts of the PCB wrapped around the receiver. Similarly, a flab may be folded in front (or a side-fire LED) to allow an emitter to shine inwards, or a flap parallel to the receiver making connections to the RITE-wire or receiver easier. One may imagine many variations to the geometry to the flex PCB and the illustrated examples should just be seen as mere example configurations.

In an embodiment, where the sensors, especially a PPG sensor is considered in a behind the ear hearing aid (i.e. a BTE type hearing aid), it is important to consider for example the risk of disturbances from e.g. external light sources. An example of a BTE type hearing aid comprising PPG sensors is illustrated in FIG. 15. When having a sensor, such as a PPG sensor in a BTE style hearing aid, the normal positioning of the LED transmitter and detector is on the axis of symmetry of the BTE hearing aid—this to achieve same performance on both ears when wearing hearing aids on both ears. The disadvantage is however that the sensors will have equal sensitivity both towards the pinna and the skull which may not be desirable. The signal may be stronger from the skull than from the pinna or vice versa. In the same manner the noise may be stronger from one side or the other.

Therefore, an alternative which achieves the same goal, as illustrated in FIG. 15 is suggested. Here the symmetry is kept intact by placing the transmitter and detector as shown in FIG. 15. One transmitter 1501 is placed on the axis of symmetry 1502 and one detector 1503 is placed on each side of the axis of symmetry 1502. It could also be chosen to place a transmitter on each side. The advantage of this arrangement compared to the known symmetrical arrangement of both LED emitter and detector is a better signal to noise ratio.

In an embodiment of the suggested solution according to FIG. 15, it is considered that the Left/Right information entered during fitting is used to select which side in the instrument the detector should be (most) active towards. The detector sensitivity direction could also be based on an estimated signal to noise ratio.

In a similar manner, it is suggested to use the Left/Right information entered during fitting to select which side in the instrument the transmitter should be (most) active towards. Further, the transmitter sensitivity direction could also be based on an estimated signal to noise ratio.

Another example could be to omit the transmitter altogether in powerful ambient light situations. Utilizing a single wavelength LED the device will only be capable of detecting blood volume changes. Moreover, in strong ambient light conditions, the transmitting LED can be ‘out shined’ by e.g. the sun. However, as the LED is present to allow enough light for the measurement, the powerful ambient light may be used instead of the transmitter, to detect the blood volume changes. This enables the detection of the blood volume signal, even when ambient conditions otherwise would not allow it (due to bright ambient conditions).

Signal Handling

The previous described embodiments, all describe how to implement sensors, such as PPG sensors, electrodes and other biometrical sensors into hearing aids of different kinds. When implementing sensors into the hearing aid, it is therefore also relevant to consider how the signals can be used and how the signals should be processed for getting the right information from the detected signals.

Several electrophysiological signals like, electroencephalogram, electrocardiogram, electrooculogram, and skin conductance can be measured from within the ear cavity by attaching electrodes to the parts of the ear canal, in a particular configuration and in a particular location in the ear cavity. However, a compromise needs to be made when deciding key parameters for the signal of interest. These include but are not limited to signal pre-conditioning, hardware bandwidth, amplification strategy, electrode location, among others. Accordingly, it is necessary to have a system that can dynamically adjust these parameters in order to obtain the optimal configuration mode for each electrophysiological signal.

Figure 10:
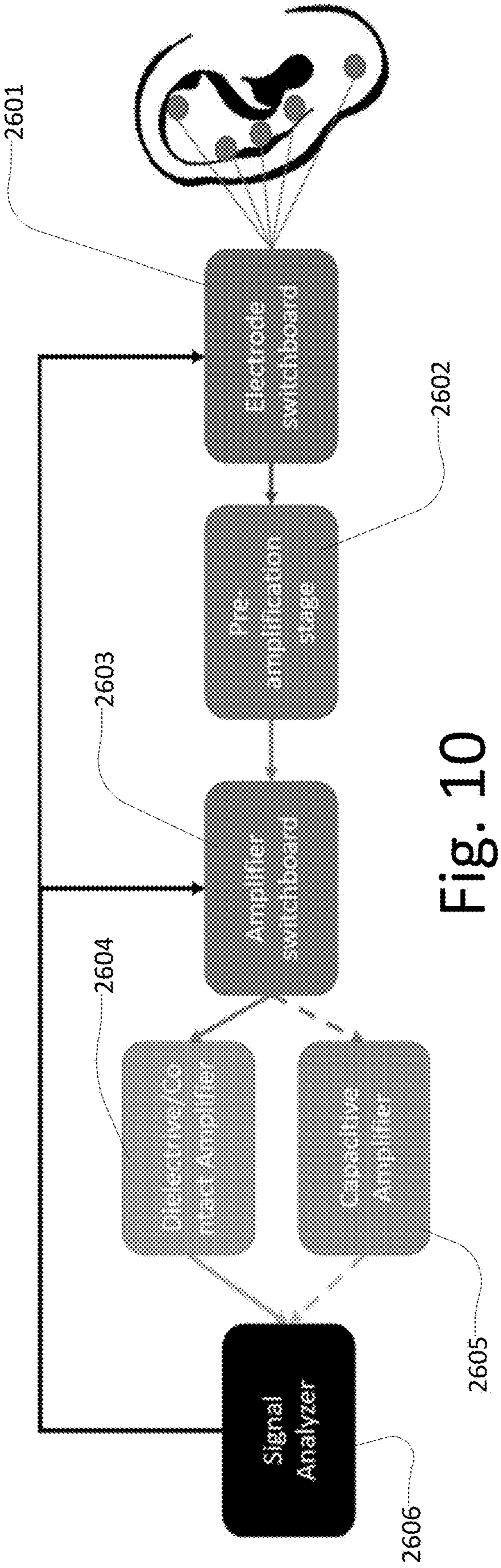
FIG. 10 illustrates an example of signal processing of electrode sensors connected to a hearing aid.

Therefore, in one embodiment illustrated in FIG. 10, especially when considering electrode sensors, a signal handling solution, where an electrode switchboard 2601 creating two or more electrode configurations by combining the available electrodes into different groups or one single electrode, is considered. The electrode switchboard 2601 is in communication with a pre-amplifier, which at an pre-amplification stage 2602 is configured for conditioning the recorded electrode signals before amplification. Further, the pre-amplifier 2602 is in electrical communication with an amplifier switchboard 2603 that is configured to interphase the output of the electrode switchboard to two different instrumentation amplifiers. The two instrumentation amplifiers is configured with one for dielectric or contact electrode input 2604 and one for capacitive electrode inputs 2605, and is further in electrical communication with a signal analyser 2606 that is configured to evaluate the noise level, signal amplitude and electrode contact from each possible configuration of the electrodes and as an output choose the optimal configuration for measuring in a given scenario (i.e., feedback loop to electrode switchboard and amplifier switchboard to optimize signal quality). This general setup is illustrated in FIG. 10, in a schematic setup. It should be noted that the electrodes (or other types of sensors) are illustrated to be positioned in the concha of the ear. This is a real possibility but as described throughout the disclosure, these electrodes can also be arranged within the ear canal in close contact to the skin of the ear canal via the hearing aid parts positioned therein.

EXAMPLE APPLICATIONS

As is already indicated throughout the disclosure, different applications for different kinds of sensors have been considered, where a chosen selection will be explained in the following in connection with signal handling of the sensor data.

An application considered when using a PPG sensor in a hearing aid is for example to use the PPG sensor recordings to evaluate if a hearing aid is positioned on the ear or not. This is used to for example be able to turn off the hearing aid, when it is not being worn, and further to collect information on how the hearing instrument is being used.

Figure 11:
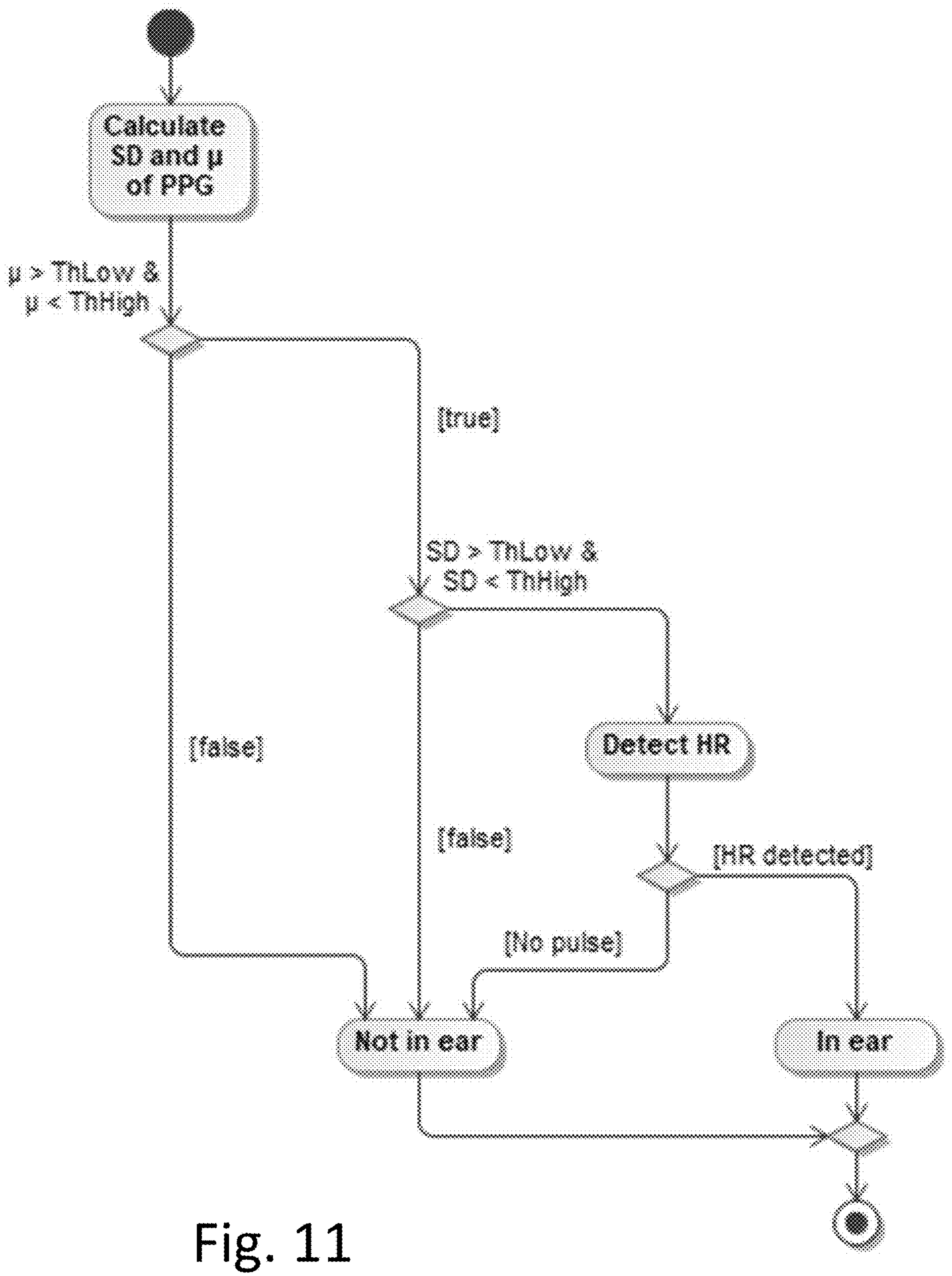
FIG. 11 illustrates example signal processing steps in connection with a PPG sensor of a hearing aid.

That is, in an embodiment, the PPG sensor may be used as an on-ear wear detector, as it has been found that the mean value (μ) and standard deviation (SD) of a photoplethysmography (PPG) sensor are significantly different when the sensor is placed on human skin compared to a table/free space. These values can therefore be used to give an estimate of whether the sensor is in the ear or not. Further, if the and SD are within bounds, the algorithm may be configured to detect a heart rate (HR). If no HR is found, the sensor is evaluated to be outside the ear and the opposite if the HR is found. Thus, when placing a PPG sensor in the hearing instrument these measures can be used to detect wearing of the HI. The process is shown in FIG. 11. Here it can be seen that if the mean value (μ) is within a set threshold range (i.e. μ>ThLow & μ<ThHigh) then it is evaluated in the standard deviation (SD) is within a set threshold range (i.e. SD>ThLow & SD<ThHigh) and if this is true the heart rate (HR) may be detected. If a heart rate is detected, then it is evaluated that the hearing aid is in the ear, whereas if the heart rate is not detected, or the mean value (μ) or the standard deviation (SD) is out of the set threshold ranges, then the hearing aid is evaluated not to be in the ear.

Figure 12:
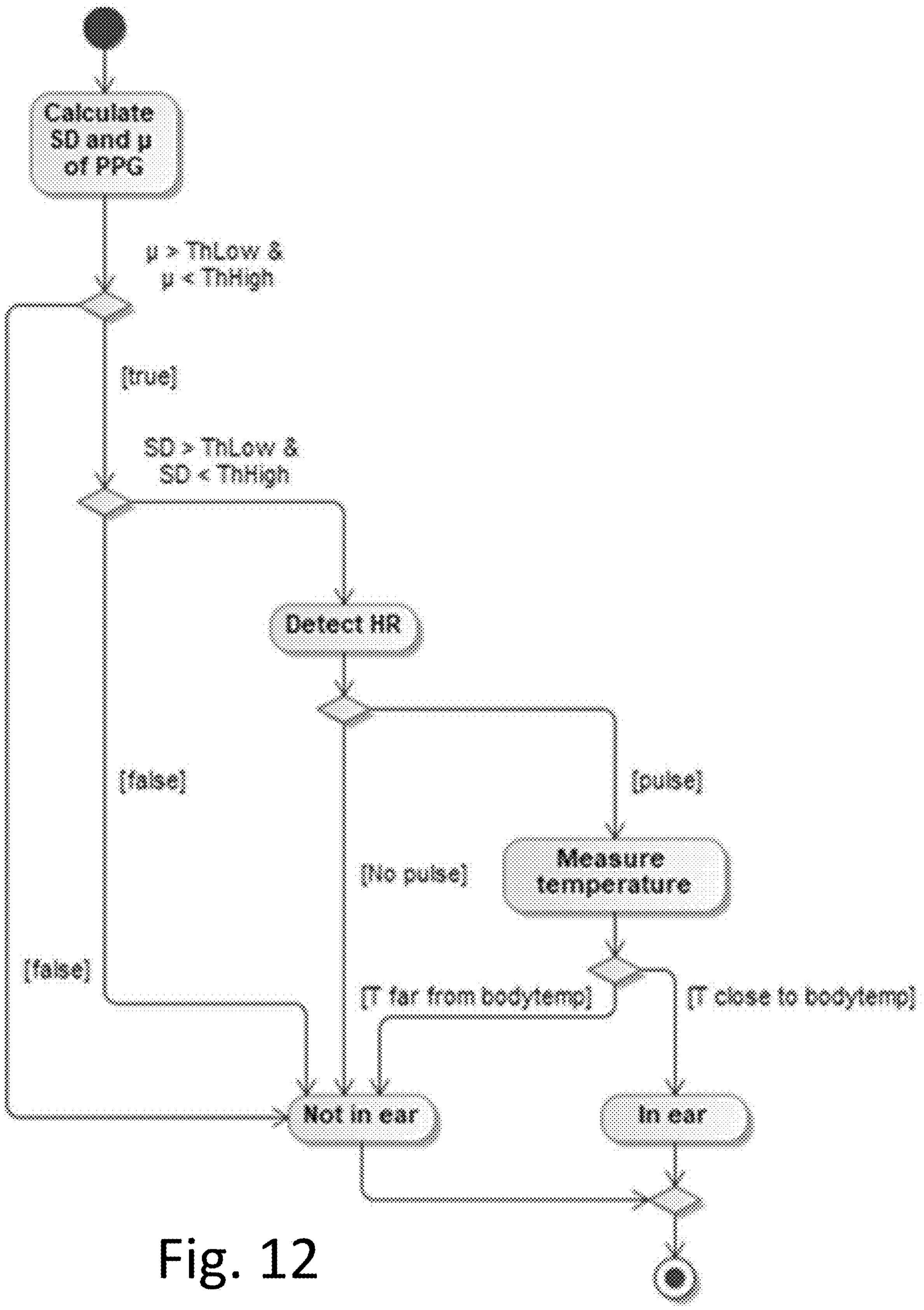
FIG. 12 illustrates example signal processing steps in connection with a PPG sensor and a temperature sensor of a hearing aid.

In a further development, other possible biomedical sensors, such as temperature sensors may be included in the process as well, when mounted in a hearing to improve the estimate of wear detection. This process is illustrated in FIG. 12. As illustrated the process is as previously described in relation to FIG. 11 in addition to the step that when a heart rate is detected a further step of controlling the temperature by a temperature sensor is included. Thus, as seen in FIG. 12, if the temperature from the temperature sensor is detected to be close to body temperature and if a heart rate is also detected, then the hearing aid is deemed as being placed in or at the ear. In any other cases, as also illustrated in FIG. 12, the hearing aid is evaluated not to be positioned in the ear. Thus, by including e.g. the temperature sensor, a more robust wear detection is achieved, since it relies on two biometrical parameters for evaluating if the hearing aid is worn.

In general, the placement of sensors within the ear allows for different biometrical measurement of a person wearing a hearing aid. However, when evaluating the detected signals, it is relevant to ensure that the signals correctly "spots" the biometrical measure in order not to inform about any false information, such as false alarms on e.g. heart rate, temperature or other relevant biometrical measurements. Furthermore, noise components from the sensors, which preferably also should be avoided is motion artifacts and other noise components.

Therefore, in one embodiment, it has been considered how to evaluate the signal quality of a sensor, especially for the following described example, a PPG sensor. Thus, in the following it will be described how to take advantage of a multi-channel PPG sensor for estimating a physiological parameter based on signal quality index (SQI) estimation. Signal quality estimation provides a measurement of how confident a signal reading can be considered, and when using a multichannel system, one is able to choose which of the multichannel signals to use and react to. This reduces the false alarm rates/false predictions of the measurements performed by the sensor. A multi-path PPG system design has advantages over single channel PPG systems. It is possible to get redundant PPG data, thus enabling more noise supressed data which are crucial for any PPG derived physiological parameter estimation. However, in some cases, (e.g. motion/jaw movement), averaging out all multipath data degrade the overall signal due to huge transient effect of motion. In that case it is necessary to either 1) choose the signal channel being least corrupted by motion, or 2) Execute motion compensation algorithm to suppress the motion artefact.

In FIG. 13 a four-channel PPG signal is used for the hearing aid instrument as an example. By using a four-channel PPG signal it is possible to determine which of the channels has the best signal quality and hence, increase the accuracy of the derived metrics from the PPG signal using a signal quality index (SQI). The SQI may be configured on the basis of at least one of three different methods: Dynamic Time Warping (DTW), Direct matching and/or linear resampling. The three methods are compared to a template which is generated from the PPG beats.

In more detail, FIG. 13 show the process of finding the optimal signal channel to be used for the biometrical measures. That is, the recorded data 2900 from the sensor signal (in this case a PPG sensor), is firstly preprocessed 2901. In the preprocessing step 2901 a band pass filter, which passes frequencies between [0.5 10] Hz, is implemented. The signals are then normalized to the [0.05, 0.95] quantiles, this is done in order to make the signal less noise prone and make it easier and more consistent to find the PPG peaks which is the final step in the pre-processing step.

For the SQI function to work, either a PPG waveform (beat) template has to be input to the function, otherwise an initial template is generated by averaging every beat in a 30 second window. Then this initial template (T1) is updated and recalibrated by all the PPG beats with a cross correlation coefficient>0.8, resulting in the new template (T2). If more than half the beats in the 30 second window was removed in order to generate template T2, it is deemed untrustworthy, and the template from the previous window will be used. If no previous window is available, the new 30 seconds will be used instead. This is what happens in the template process 2902 of FIG. 13.

Dynamic Time Warping (DTW) is then used to correlate two time series with each other. DTW allows for nonlinear and nonstationary changes in the beat morphology, and makes it possible to correlate each beat with the template, see step 2903 in FIG. 13. Accordingly, DTW finds the optimal path in order to minimize the cumulative distance of the path, see FIG. 13A. Here, the DTW process is illustrated in more detail. That is, FIG. 13A(a) illustrates a PPG template (T, bold) and a recorded PPG beat (B, Normal line). FIG. 13A(b) illustrates the alignment between the template (T) and the recorded beat (B) whereby a warping matrix can be constructed to find the optimal path minizing the distance between the recorded beat (B) and the template (T). FIG. 13A(c) illustrated the alignment flow between the template (T) and the recorded beat (B). The direct matching method is in more detail, done by selecting the sampling point series of each beat within the 30 second window, starting at the onset of the beat and ending at the length of the template. Then calculating the correlation coefficient with the template as the direct matching. Another method, i.e. Linear resampling is done by selecting each beat between two PPG onsets and linearly stretch (stretch or compress depending on if the beat length is longer or shorter than the template, respectively). Then calculate the correlation coefficient as the linear resampling.

Preferably all three methods are used in the SQI calculation by averaging the three methods, thereby resulting in an SQI per beat. This is illustrated in FIG. 13B. This output, as illustrated in FIG. 13B indicates which channel is getting the highest signal quality, hence making it possible to automatically switch to the channel with the highest SQI, resulting in more confident PPG estimates.

FIG. 13C illustrates examples of an SQI index calculated from a signal captured in different photo detectors (PD) from two LEDs (in a 2 LED+2 PD setting). It can be seen from the figure that, data at PD1 exhibits higher SQI than the PD2 which is more corrupted by noise. Hence it is preferable to calculate estimates from the PD1 data only and ignoring data from the PD2.

A further component which preferably should be compensated for when detecting biometrical signals from sensors in connection with a hearing aid having the sensors positioned substantially in the ear canal, is motion artifacts. A solution to this is given in this disclosure by utilizing a motion compensation algorithm based on Constrained Independent Component Analysis (cICA). An example is given in FIG. 13D, where a corrupted Ear-PPG data set has been enhanced, by using a motion component algorithm. FIG. 13D in more detail illustrates a shaded area 2905 of the signal, where motion is present. As seen in the Figure the algorithm uses a template 2906 calculated from the cICA and uses that template to motion compensate the PPG signal, resulting in the signal 2907 of the Figure. Thus, as illustrated in the motion component 2908 can be found and compensated for in the original PPG signal. However, in some cases the motion artifact cannot be compensated for by using the just described algorithm, and therefore other solutions have been suggested in this disclosure.

That is, as illustrated in FIG. 13E, a model for PPG motion compensation based on the previously described SQI is presented. The motion compensation algorithm is run on the segment of data having a moderate SQI, below which the data is completely unusable and therefore discarded as shown is FIG. 13E. That is, as illustrated in FIG. 13E, the PPG data is sent into the preprocessing step as previously described in relation to FIG. 13. The SQI, as also previously described is then calculated and the SQI's are divided into three thresholds, i.e. motion compensation necessary (50<SQI<80), no motion compensation needed (80<SQI), discard signal (50<SQI). The SQI signals needing motion compensation is run through a motion compensation algorithm as described in relation to FIG. 13D, whereas the other signals are discarded or used direction as a clean signal which can be directly used. The motion compensation is thus calculated on already SQI evaluated signals, i.e. the signals that need motion compensation based on the SQI classification, is given a motion compensation and then compared to the original signals, thereby removing the motion artifact from the signal. An example is illustrated in FIG. 13F, where it is seen that the motion corrupted data (i.e. a signal having an SQI between 50 and 80)) is run through the motion compensation calculation whereby the motion component can be identified and removed from the signal. The example shown in FIG. 13F illustrated a part of the data, based on the interval [7500 8500], as being discarded due to poor SQI (<50) to ensure the highest quality data to be used for any potential physiological marker estimation. The remaining of the data from the PPG sensor was motion compensated as described in the framework of FIG. 13F.

In another suggested exampled for detecting and correcting for motion artifacts arising from sensors positioned in relation to a hearing aid in the ear canal of a user, the suggestion is to utilize not only a PPG sensor but also an EEG sensor (or similar sensor). Thus, in an embodiment, the hearing aid is configured to transmit biometrical sensor data to the auxiliary device via the communication interface, and wherein the auxiliary device is configured to process said biometrical sensor data in a signal processor of the auxiliary device and to transmit an output from said data processing back to said hearing aid.

In one embodiment, the biometrical sensor data transmitted to the auxiliary device is transmitted to said signal processor of the auxiliary device, wherein the signal processor is configured to perform a pre-processing step of the biometrical data and calculate a signal quality index on the pre-processed data to evaluate the biometrical signal data with the highest quality, and wherein the biometrical signal data is motion compensated prior to calculating the signal quality index. An example of a motion compensation of a biometrical signal recorded from the ear canal will be explained in more detail in the following.

That is, it is in the following proposed to detect motion onset based on both EEG and PPG sensor data, e.g. transmitted to an auxiliary device for processing. Motion generating from physical activity result in the change of the sensor placement relative to the skin, which corrupts the data as artefact noise. FIG. 14A and FIG. 14B show typical motion artefact independently acquired from EarEEG and PPG signals, respectively, inside the ear canal.

Motion in the EarEEG can be characterized by capturing eye movement, i.e. measuring the EOG signal. The EarEEG level changes with saccade eye movement proportionally. However, an EarEEG signal is prone to slow drift which is removed by a high pass filter at a preprocessing step. Normal head rotation induce vexibulo ocular reflex in the EarEEG which is basically the fact that eye rotates faster than the head, essentially EOG signal. This specific phenomenon can be used to flag the PPG data during head rotation and by identifying the flagged data, special filter/artefact compensator can be designed.

That is, one way to characterize the motion in the EEG is by utilizing an Extended Kalman filter. A random motion in the data will exhibit higher residual in the measurement update step. The residual value over a certain threshold would flag the data as motion corrupted. Accordingly, in a method illustrated in FIG. 14C using both EEG data and PPG for compensating the PPG signal, the EarEEG is measured and the PPG signal is measured. The EarEEG signal is run through a motion detector, where motion is detected as described above. If motion is detected, the detected motion is used in the PPG data before calculating the previously described SQI. If motion is not detected the data from the PPG can be seen as "clean signal" and the SQI is calculated based on the "clean signal". In both cases a motion compensated PPG signal can be calculated.

The motion detector used on the EEG signal is in more detail illustrated in FIG. 30D, where it is seen that the EEG signal is input to a motion detection block, where the signal is processed by a Kalman filter state with constant velocity. The residual is found and if the residual is above a set threshold motion is detected, and if not, motion is not detected. The outcome, motion/no motion is input to evaluate the PPG signal as previously described.

In one application of the different kind of sensors considered in view of the solutions described, the PPG sensor has also been considered to be utilized for measuring the amount of light a person wearing the hearing aid is exposed to. That is, in one embodiment, the hearing aid is configured with a light sensor, for example a PPG sensor, positioned at an environmental facing surface of the hearing aid. In this way it may be possible to e.g. detect light to evaluate risk of epileptic seizures, securing a good sleep, that is to assess if the type of light exposure is the right color and intensity at the right time of day, decreasing risk of sun-burning by comparing light exposure to local UV-index and/or asses if the user gets enough light exposure during the day (vitamin D).

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

The invention claimed is:

1. A hearing aid having one or more biometrical sensors, the hearing aid comprising:
- at least one microphone configured to receive a sound of the surroundings;
- a signal processor configured to process the sound received from the microphone;
- a speaker unit configuration configured to emit the processed sound into the ear of a user;
- a dome configured to be positioned into the ear of the user, the speaker unit configuration being configured to be inserted into the dome;
- wherein the one or more sensors are configured as biometrical sensors configured for recording health data of a hearing aid user;
- wherein the one or more sensors are configured to be incorporated into the dome material of the hearing aid.

2. The hearing aid according to claim 1, wherein the dome is soft gel-based and is configured with conductive particles.

3. The hearing aid according to claim 2, wherein the soft gel-based dome is configured to be constructed with an oxide material that act as a flexible-dry contact electrode configured to record bioelectric signals from the ear of the user.

4. The hearing aid according to claim 2, wherein the conductive particles are configured to be disposed in the gel material of the dome on a uniform distribution, to create a single recording electrode.

5. The hearing aid according to claim 2, wherein the conductive particles are configured to be disposed in the gel material of the dome in separate deposition clusters, to create multiple recording sites.

6. The hearing aid according to claim 2, wherein the dome comprises a plurality of metal oxide particle pockets, each having oxide metal particles therein to create a dry-contact electrode in the dome.

7. The hearing aid according to claim 6, wherein the particle pockets are configured to be in communicative contact with a single collector, thereby creating a single electrode with a plurality of contact points via the particle pockets.

8. The hearing aid according to claim 6, wherein each of the particle pockets is configured to be connected to a separate collector, thereby creating a plurality of separate electrodes.

9. The hearing aid according to claim 1, further comprising a behind the ear housing comprising a ground electrode and a reference electrode.

10. The hearing aid according to claim 1, wherein the one or more sensors are configured for recording electroencephalogram signals.

11. The hearing aid according to claim 1, wherein the hearing aid is configured to transmit biometrical sensor data to an auxiliary device via a communication interface, and is configured to receive an output from a data processing of said biometrical sensor data in a signal processor of the auxiliary device.

12. A hearing system comprising a hearing aid according to claim 1 and an auxiliary device, wherein the auxiliary device comprises:

a communication interface configured to receive biometrical sensor data from the hearing aid; and a signal processor configured to:

perform a pre-processing step of the biometrical data; and calculate a signal quality index on the pre-processed data to evaluate the biometrical signal data with the highest quality, wherein the biometrical signal data is motion compensated prior to calculating the signal quality index.

13. The hearing system according to claim 12, wherein the signal processor of the auxiliary device is configured to characterize motion in the biometrical signal data by using a Kalman filter.

14. The hearing system according to claim 13, wherein the biometrical signal data is processed using a Kalman filter state with constant velocity, to find a residual, motion being detected if the residual is above a set threshold.

* * * * *